US010524973B2

(12) United States Patent
Sodeyama et al.

(10) Patent No.: US 10,524,973 B2
(45) Date of Patent: Jan. 7, 2020

(54) MOVEMENT ASSISTANCE DEVICE

(71) Applicant: HONDA MOTOR CO., LTD., Minato-Ku, Tokyo (JP)

(72) Inventors: Yoshinao Sodeyama, Saitama (JP); Toru Takenaka, Saitama (JP); Hiroshi Gomi, Saitama (JP); Yosuke Ikedo, Saitama (JP); Kenichi Katagiri, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 268 days.

(21) Appl. No.: 15/539,673

(22) PCT Filed: Dec. 17, 2015

(86) PCT No.: PCT/JP2015/085380
§ 371 (c)(1),
(2) Date: Jun. 24, 2017

(87) PCT Pub. No.: WO2016/104330
PCT Pub. Date: Jun. 30, 2016

(65) Prior Publication Data
US 2017/0360645 A1    Dec. 21, 2017

(30) Foreign Application Priority Data

Dec. 26, 2014    (JP) .................................. 2014-266598

(51) Int. Cl.
*A61H 3/00*    (2006.01)
*A61H 1/02*    (2006.01)
(Continued)

(52) U.S. Cl.
CPC ................. *A61H 3/00* (2013.01); *A61F 2/68* (2013.01); *A61H 1/024* (2013.01); *A61H 1/0244* (2013.01);
(Continued)

(58) Field of Classification Search
CPC ... A61H 3/00; A61H 1/00; A61H 1/02; A61H 1/024; A61F 2/60; A61F 2/64; A61F 2/68;
(Continued)

(56) References Cited

U.S. PATENT DOCUMENTS 9,351,900 B2    5/2016  Walsh et al.
2006/0167546 A1*  7/2006  Bartlett .................... A61F 2/60
                                           623/11.11
(Continued)

FOREIGN PATENT DOCUMENTS

JP     2012-090758 A    5/2012
JP     2012-235928 A   12/2012
(Continued)

*Primary Examiner* — Suba Ganesan
*Assistant Examiner* — Aren Patel
(74) *Attorney, Agent, or Firm* — Carrier Blackman & Associates, P.C.; Joseph P. Carrier; Jeffrey T. Gedeon

(57) ABSTRACT

A movement assistance device is provided with thigh frames, lower leg frames, and knee joint mechanisms which are disposed on the outer side and the inner side, respectively, of each knee of a person to be assisted. Each of the thigh frames has a first main frame, which extends in the longitudinal direction of a thigh from a base disposed on one side of the hip of the person to be assisted to the outer knee joint mechanism, a second main frame, which obliquely extends on the front side of the thigh from the base to the inner knee joint mechanism, and a body support member, which is extended between the two main frames on the rear surface side of the thigh.

19 Claims, 14 Drawing Sheets

(51) Int. Cl.
- *B25J 9/00* (2006.01)
- *B25J 9/12* (2006.01)
- *B25J 13/08* (2006.01)
- *B25J 9/10* (2006.01)
- *A61F 2/68* (2006.01)
- *A61F 2/70* (2006.01)

(52) U.S. Cl.
CPC ........... *B25J 9/0006* (2013.01); *B25J 9/1045* (2013.01); *B25J 9/126* (2013.01); *B25J 13/085* (2013.01); *B25J 13/088* (2013.01); *A61F 2002/701* (2013.01); *A61H 2201/123* (2013.01); *A61H 2201/1215* (2013.01); *A61H 2201/165* (2013.01); *A61H 2201/5058* (2013.01); *A61H 2201/5061* (2013.01); *A61H 2205/10* (2013.01); *A61H 2205/102* (2013.01)

(58) Field of Classification Search
CPC ........ B25J 9/0006; B25J 9/1045; B25J 9/126; B25J 13/085
USPC .......................................... 601/5, 35; 623/24
See application file for complete search history.

(56) References Cited

U.S. PATENT DOCUMENTS

| | | | |
|---|---|---|---|
| 2010/0063424 A1* | 3/2010 | Kudoh | A61H 3/008 601/35 |
| 2012/0271207 A1 | 10/2012 | Shoen et al. | |
| 2013/0012852 A1* | 1/2013 | Imaida | A61F 5/01 602/16 |
| 2013/0226048 A1* | 8/2013 | Unluhisarcikli | A61H 3/00 601/34 |
| 2014/0024978 A1* | 1/2014 | Killian | A61H 1/0244 601/33 |
| 2014/0046235 A1* | 2/2014 | DeSousa | A61F 5/0123 602/16 |
| 2014/0148738 A1* | 5/2014 | Nagasaka | A61H 3/00 601/35 |
| 2014/0163435 A1 | 6/2014 | Yamamoto et al. | |

FOREIGN PATENT DOCUMENTS

| | | |
|---|---|---|
| JP | 2014-018536 A | 2/2014 |
| JP | 2014-054526 A | 3/2014 |
| JP | 2014-508010 A | 4/2014 |
| JP | 2015-529574 A | 10/2015 |

* cited by examiner

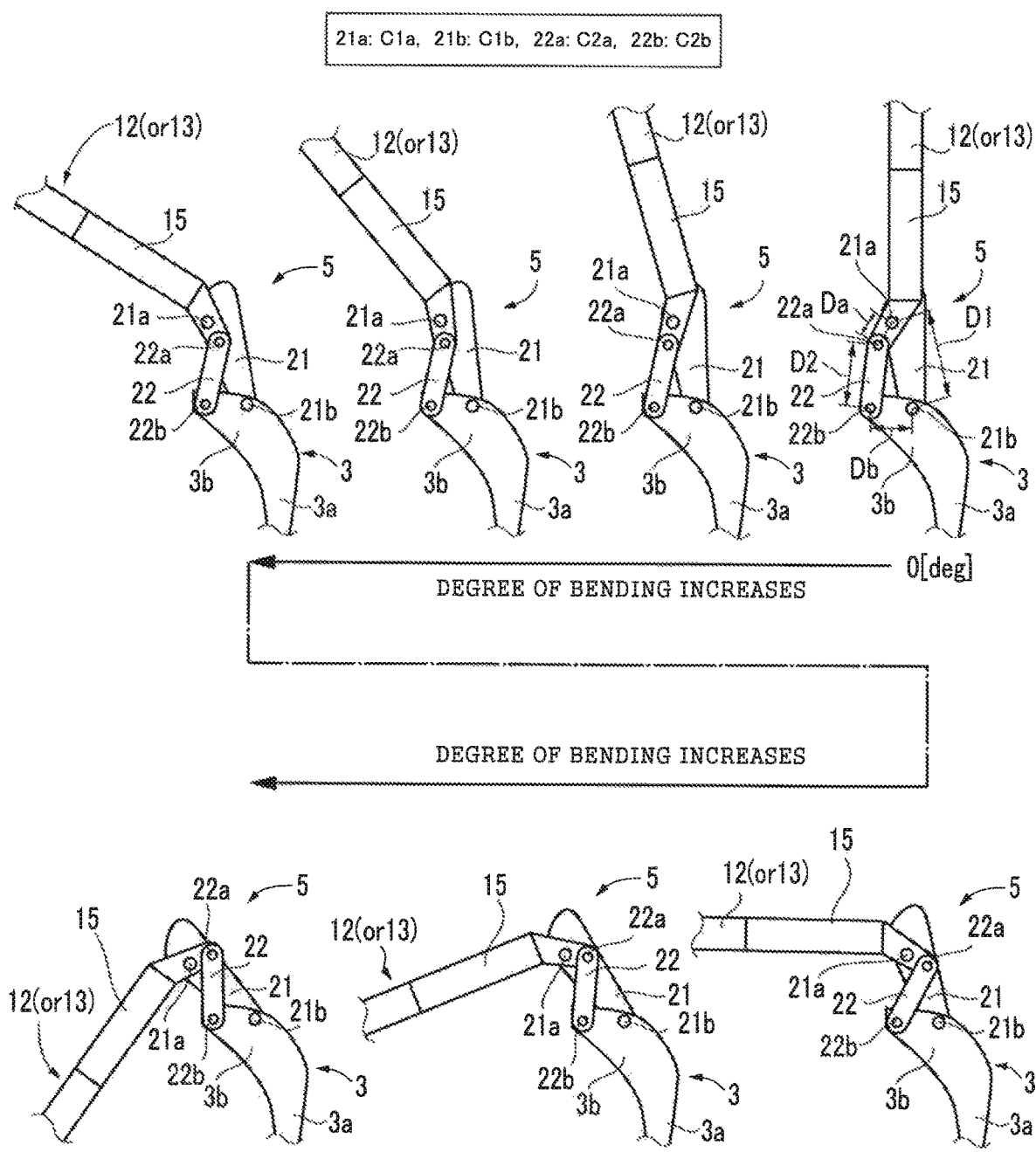

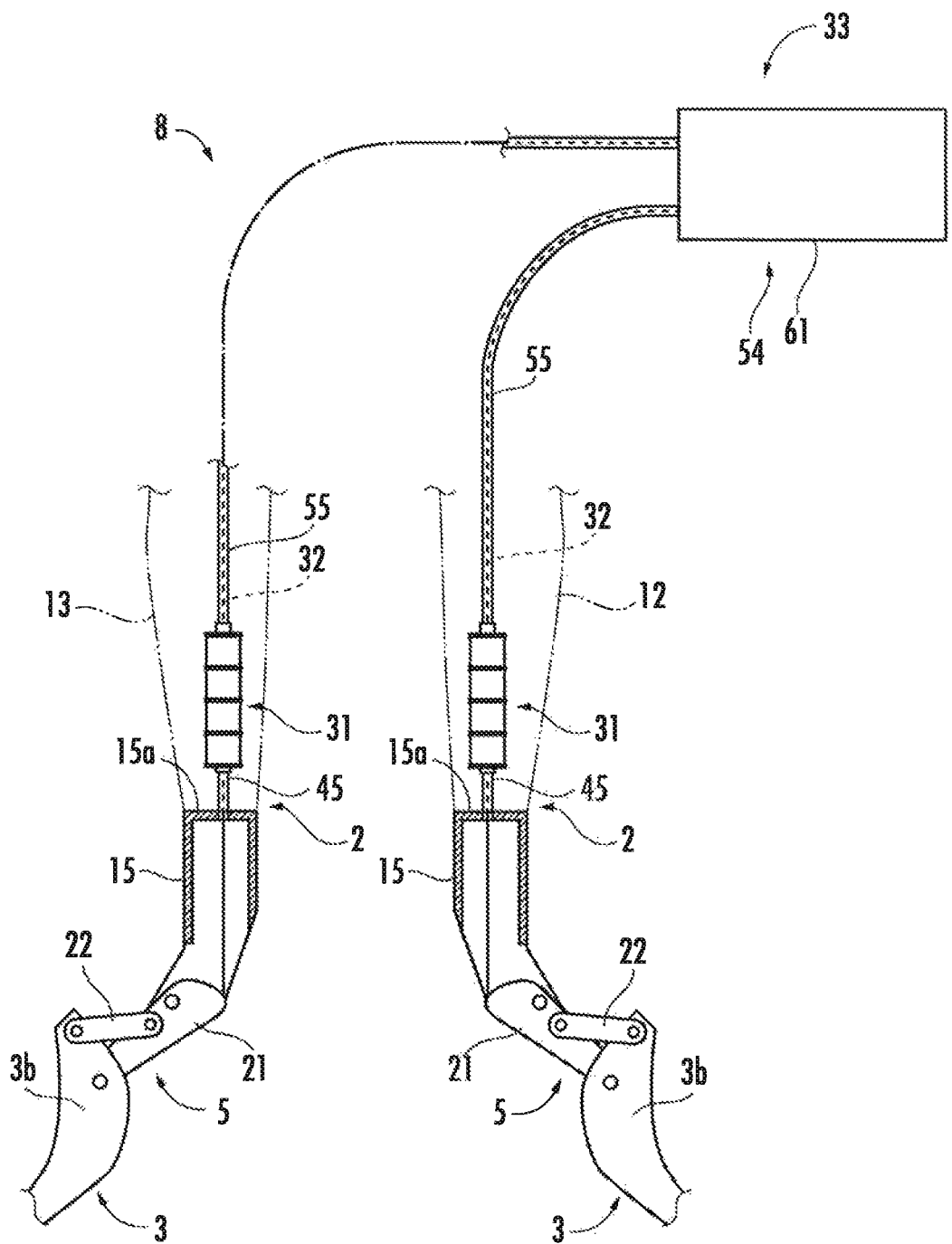

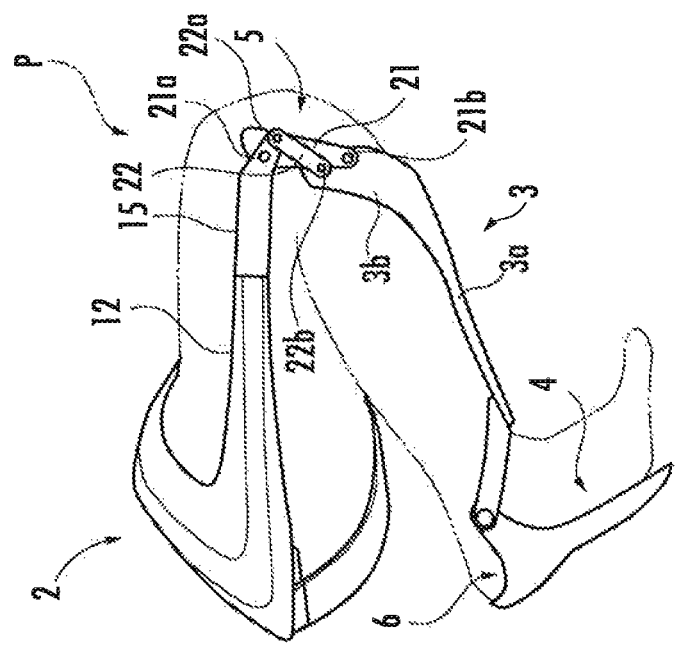
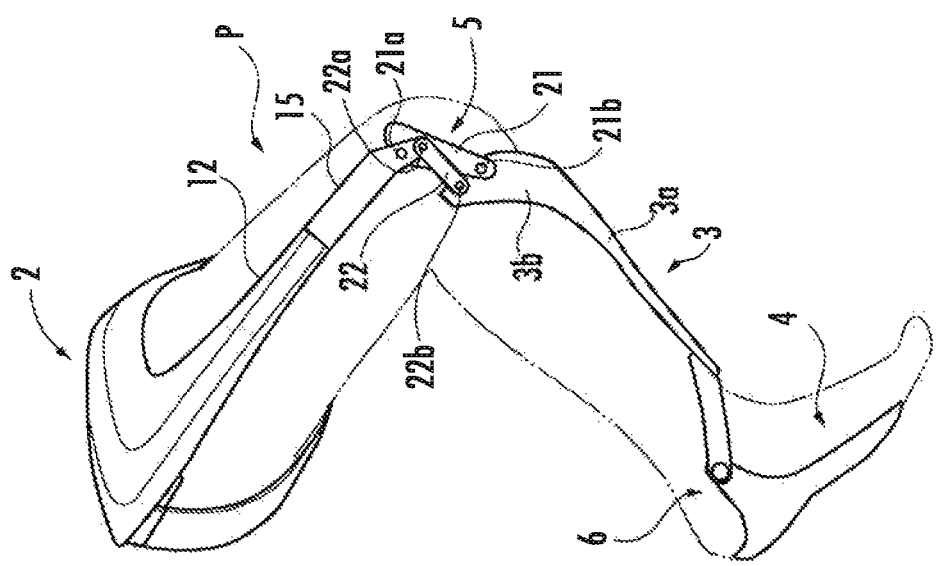
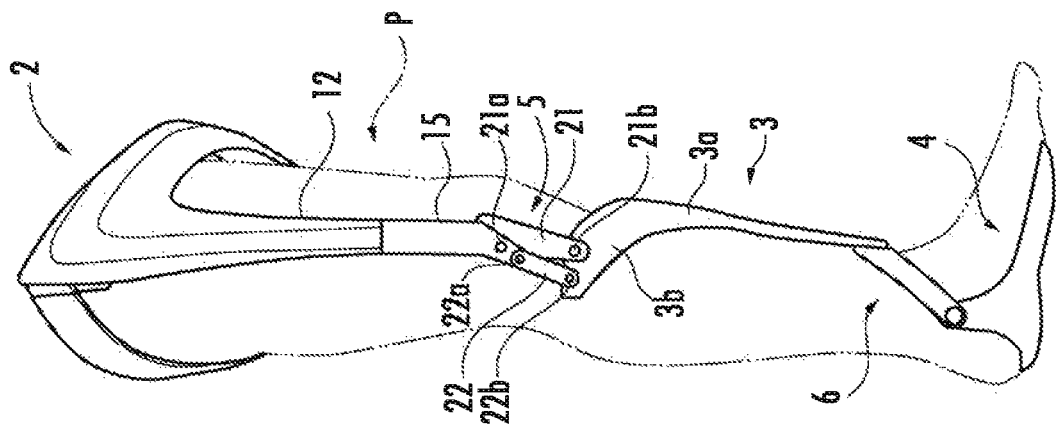

MOVEMENT ASSISTANCE DEVICE

TECHNICAL FIELD

The present invention relates to a movement assistance device adapted to be attached to a person to be assisted.

BACKGROUND ART

There has conventionally been known a movement assistance device configured to be attached to the legs of a person (human being) to be assisted and to generate power to assist the bending and stretching of his or her legs. For example, Japanese Patent Application Laid-Open No. 2014-508010 (hereinafter referred to as "Patent Literature 1") discloses a movement assistance device which has a thigh frame and a lower leg frame to be attached to the thigh and the lower leg, respectively, of each leg of the person to be assisted, and a spring. The movement assistance device is configured to apply power to a joint mechanism between the thigh frame and the lower leg frame by the elastic force of the spring, thereby assisting the movement of the leg.

SUMMARY OF INVENTION

Technical Problem

According to the movement assistance device described in Patent Literature 1, the thigh frame and the lower leg frame are attached to a thigh and a lower leg, respectively, of a person to be assisted by band-shaped members, such as belts, which are wrapped around his or her thigh and lower leg.

In the movement assistance device having the foregoing structure, the band-shaped members generally have to be relatively soft in order to enhance the accuracy of fit between the band-shaped members wrapped around a thigh and a lower leg of a person to be assisted and the thigh and the lower leg.

However, using such soft band-shaped members to be wrapped around a thigh and a lower leg inconveniently causes the band-shaped members to excessively bend when, for example, an assistance force in a direction for lifting the upper body of a person to be assisted is applied to the person from the movement assistance device (i.e. when power in the direction for stretching the thigh frame and the lower leg frame is applied to the joint mechanism between the two frames). This tends to result in a situation in which an assistance force in an appropriate direction cannot be applied to the person to be assisted.

Further, the band-shaped members tend to dig into thighs and lower legs and may therefore cause the person to be assisted to develop tight feeling or discomfort.

Further, according to the structure of the movement assistance device described in Patent Literature 1, the thigh frame and the lower leg frame are placed only on the outer side of a leg of a person to be assisted. Hence, when an assistance force is applied to the person to be assisted, the thigh frame or the lower leg frame tends to curve. This tends to result in an inadequate assistance force acting on the person to be assisted or an inappropriately directed assistance force.

In addition, the joint mechanism between the thigh frame and the lower leg frame is apt to be dislocated relative to a knee joint of the person to be assisted. This may cause the bending movement between the thigh frame and the lower leg frame to be out of synchronization with the bending movement of a leg of the person to be assisted, thus preventing the smooth bending of the leg of the person to be assisted.

The present invention has been made in view of the above background, and an object of the invention is to provide a movement assistance device which can be attached to a person to be assisted with an appropriate accuracy of fit and which makes it possible to properly apply, to a person to be assisted, a force for assisting the movement of the legs of the person to be assisted.

Solution to Problem

To this end, a movement assistance device in accordance with the present invention is a movement assistance device including: a thigh frame; a lower leg frame; a knee joint mechanism which bendably connects the thigh frame and the lower leg frame; and a joint power generator which generates joint power, which is the power to be imparted to the knee joint mechanism, the movement assistance device being attached to a person to be assisted such that the thigh frame and the lower leg frame move integrally with a thigh and a lower leg, respectively, of a leg of the person to be assisted, wherein the knee joint mechanism is composed of two knee joint mechanisms disposed on both inner and outer sides of the knee of the leg of the person to be assisted, the thigh frame has a first main frame and a second main frame, which extend in a bifurcated manner, from a base disposed on the outer side of art upper portion of the thigh of the leg of the person to be assisted P or on one side of a hip of the person to be assisted P and which connect the base to a joint mechanism on an outer side of the knee and a joint mechanism on an inner side thereof, respectively, and a body support member which is extended between the first main frame or the base and the second main frame, the first main frame is configured to extend from the base in a longitudinal direction of the thigh along an outer side surface of the thigh to the joint mechanism on the outer side of the knee, the second main frame is configured to extend from the base to the joint mechanism on the inner side of the knee via a front surface side of the thigh, and to extend from the base obliquely with respect to the thigh in a direction toward the joint mechanism on the inner side of the knee, as observed from a front side of the thigh, and the body support member is configured to extend along a rear surface of the thigh between a portion of the first main frame, which portion is on a lower side with respect to the base, or the base and a portion of the second main frame, which portion is on a lower side with respect to the base, and to be in contact with the rear surface (a first aspect of the invention).

In the present invention, the phrase "one side of the hip of the person to be assisted" related to the location of the base of the thigh frame means the left side of the hip of the person to be assisted in the case of the thigh frame for the left leg of the person to be assisted, and means the right side of the hip of the person to be assisted in the case of the thigh frame for the right leg of the person to be assisted.

Further, the phrase "the thigh frame moves integrally with a thigh of a leg of the person to be assisted" means that the thigh frame moves together with the thigh of the leg so as to maintain the position and the attitude of the thigh frame with respect to the thigh of the leg to be constant or approximately constant. In this case, a slight change in the position or the attitude of the thigh frame with respect to the thigh of the leg caused by a movement of the leg (a slight relative displacement of the thigh frame with respect to the thigh of the leg) can be allowed. The same applies to a phrase "the lower leg frame moves integrally with the lower leg of the leg of the person to be assisted."

According to the first aspect of the invention, the thigh frame has the first main frame and the second main frame. This provides the thigh frame with high bending stiffness in a pitch direction (the bending stiffness about an axis in the lateral direction of a thigh of the person to be assisted to which the thigh frame is attached).

With this arrangement, when the joint power is imparted to the knee joint mechanism at the time of, for example, bending or stretching the leg of the person to be assisted to which the thigh frame and the lower leg frame have been attached, the contact between the body support member and the thigh of the leg of the person to be assisted will be highly stable. This enables stable transmission of a required assistance force from the movement assistance device to the person to be assisted.

For example, in a state in which the leg of the person to be assisted to which the thigh frame and the lower leg frame have been attached is in contact with a ground (more specifically in a state in which the leg is in contact with a ground so as to be subjected to a reaction force against the gravitational force acting on the person to be assisted), when joint power in a direction for stretching the thigh frame and the lower leg frame is imparted, with the leg bent, to the knee joint mechanism, a translational force in a direction for pushing up the upper body of the person to be assisted (an upward translational force), i.e. an assistance force for stretching the leg of the person to be assisted, can be applied with high stability from the movement assistance device to the person to be assisted through the intermediary of the body support member.

Further, the knee joint mechanism on the inner side of a knee of the person to be assisted is connected to the base through the second main frame, which extends obliquely with respect to the thigh. Thus, the thigh frame does not have a frame which extends along the inner surface of the thigh from the knee joint mechanism on the inner side of the knee to the vicinity of the base of the thigh. This arrangement prevents the thigh frame for the right or left leg of the person to be assisted from rubbing the leg on the opposite side (the left side or the right side) or interfering with the thigh frame for the leg on the opposite side.

Further, the first main frame and the second main frame of the thigh frame extend in the bifurcated manner from the base. This permits bending to allow the interval between the lower portions of the frames to change to a certain extent. Therefore, the thigh frames can be attached to thighs of various thicknesses with highly accurate fit.

Further, as described above, the contact of the body support member with the rear surface of a thigh of the person to be assisted is highly stable. This minimizes the discomfort of the person to be assisted.

Thus, according to the first aspect of the invention described above, the movement assistance device can be attached to a person to be assisted with proper fit. In addition, a force for assisting the movement of the leg of the person to be assisted can be properly applied to the person to be assisted.

In the first aspect of the invention described above, preferably, the second main frame is formed to have a curved shape so as to extend obliquely along a curved surface on a front surface side of the thigh (a second aspect of the invention).

With this arrangement, the fit of the thigh frame to a thigh of the person to be assisted can be further enhanced.

In the first aspect of the invention or the second aspect of the invention described above, preferably, the lengths in a vertical direction of the first main frame and the second main frame of the thigh frame are set such that the base portion of the thigh frame in a state in which the person to be assisted wearing the movement assistance device is standing up straight is positioned higher than a base on the inner side of a leg of the person to be assisted (a third aspect of the invention).

With this arrangement, when the leg of the person to be assisted is, for example, externally rotated at a hip joint, the possibility of the base portion of the thigh frame being pressed against the buttocks of the person to be assisted is minimized.

In the first to the third aspects of the invention described above, preferably, the lengths in a vertical direction of the thigh frame are set such that the upper end of the thigh frame in the state in which the person to be assisted wearing the movement assistance device is standing up straight is positioned lower than the hipbone of the person to be assisted (a fourth aspect of the invention).

With this arrangement, it is possible to prevent the upper body of the person be assisted and the upper end of the thigh frame from interfering with each other when the person to be assisted bends his or her upper body sideways.

In the first to the fourth aspects of the invention described above, preferably, the base portion of the thigh frame is a portion disposed on one side of the hip of the person to be assisted, and the body support member is extended between the base portion and the lower end portion of the second main frame such that the body support member is extended from the base portion obliquely with respect to the thigh frame in a direction toward the lower end portion of the second main frame (a fifth aspect of the invention).

With this arrangement, the body support member will be in contact with an area from a location on a lower side of the rear surface of the thigh of the person to be assisted to a location on an upper side thereof. Hence, when the assistance force is applied to the person to be assisted through the intermediary of the body support member, the contact pressure between the body support member and the thigh is spread. This makes it possible to prevent the way the assistance force is applied to the person to be assisted from being changed due to the degree of bending of a leg of the person to be assisted. Further, the person to be assisted can be protected from feeling a localized pressure coining from the body support member.

Especially in the case where the third aspect of the invention and the fifth aspect of the invention are combined, a place in the vicinity of the hip joint of the person to be assisted or a place in the vicinity of his or her ischial bone can be supported by the body support member. This makes it possible to ideally apply the assistance force in the direction for pushing up the upper body of the person to be assisted from the body support member.

In the first to the fifth aspects of the invention described above, preferably, in the case where the lower leg frame is formed to have two parts a1 and a2, which are connected to the knee joint mechanism on the outer side and the inner side, respectively, of the knee of the leg of the person to be assisted, and a part "b" which continues to the parts a1 and a2 and opposes a tibial tuberosity of the lower leg, the part "b" is provided with a cushioning member which is to be in contact with the tibial tuberosity of the lower leg (a sixth aspect of the invention).

With this arrangement, when, for example, the person to be assisted bends his or her leg, it is possible to prevent the part "b" of the lower leg frame from directly coming in contact with the tibial tuberosity of the lower leg while properly transmitting the force between the lower leg frame and the lower leg of the person to be assisted.

In the first to the sixth aspects of the invention described above, a configuration can be adopted, in which the movement assistance device further includes a plate-shaped foot frame having a part to be disposed on the bottom side of a foot so as to place thereon the foot of the leg of the person to be assisted, and an ankle joint mechanism which connects the foot frame to the lower end portion of the lower leg frame. In this case, the lower leg frame can be configured to extend in the longitudinal direction of the lower leg on the front side of the lower leg, and the ankle joint mechanism can be configured to have a joint shaft which relatively rotates the foot frame in a roll direction with respect to the lower leg frame and which is located above the instep of a foot of the person to be assisted, and joint shafts which relatively rotate the foot frame in a pitch direction with respect to the lower leg frame and which are located on both sides of the ankle of the leg of the person to be assisted (a seventh aspect of the invention).

In the present invention, the roll direction, the pitch direction, and a yaw direction mean a direction about a roll axis, a direction about a pitch axis, and a direction about a yaw axis, respectively, of the person to be assisted in the state in which the person to be assisted wearing the movement assistance device is standing up virtually straight. In this case, a roll axis direction, a pitch axis direction, and a yaw axis direction mean a longitudinal direction, a lateral direction, and a vertical direction, respectively, of the person to be assisted.

According to the seventh aspect of the invention, when the leg of a person to be assisted who is wearing the thigh frame, the lower leg frame, and the foot frame comes in contact with a ground, it is possible to prevent a gravitational force acting on the connecting bodies (link mechanisms) of the frames from being applied to the leg of the person to be assisted or to make it difficult for the gravitational force to be applied thereto.

In addition, when the assistance force for pushing up the upper body of the person to be assisted is generated, it is possible to prevent a reaction of the assistance force from acting on a foot. Further, a foot of the person to be assisted can be easily moved in the pitch direction or the roll direction with respect to the lower leg.

In the seventh aspect described above, preferably, the relative rotation of the foot frame in the yaw direction with respect to the lower leg frame is accomplished by twisting of the lower leg frame (an eighth aspect of the invention).

This arrangement enables the person to be assisted to easily move the foot of the leg to any attitude with respect to the lower leg. Further, there is no need to provide the ankle joint mechanism with a joint shaft in the yaw direction, thus allowing the ankle joint mechanism to have a simple configuration.

In the seventh aspect of the invention or the eighth aspect of the invention, the ankle joint mechanism may adopt a mode in which, for example, a connecting member is included, which is disposed extending in a bifurcated manner to both sides of an ankle of a person to be assisted from above the instep of a foot of the person to be assisted, a middle portion between both end portions of the connecting member is connected to a lower end portion of the lower leg frame through the intermediary of a joint shaft in the roll axis direction, and both end portions of the connecting member are connected to the foot frame through the intermediary of a joint shaft in the pitch axis direction (a ninth aspect of the invention).

This arrangement makes it possible to achieve, with an extremely simple configuration, an ankle joint mechanism which enables a foot to be easily moved with respect to the lower leg of the person to be assisted. In addition, joint shafts in the pitch axis direction are provided on both end portions of the connecting member. Thus, the stability of the attitude in the roll direction of the foot frame with respect to the lower leg frame can be enhanced.

In the seventh to the ninth aspects of the invention described above, preferably, the joint shafts in the pitch axis direction of the ankle joint mechanism are joint shafts which are inclined with respect to a horizontal plane such that an outer side of both sides of an ankle of the person to be assisted is lower than an inner side thereof in a state in which the foot frame is placed on the horizontal plane (a tenth aspect of the invention).

According to the tenth aspect of the invention, the axes of the joint shafts in the pitch axis direction of the ankle joint mechanism can be maximally matched with the central axial line of the actual rotation in a plantar flexion or a dorsal flexion of a foot of the person to be assisted. Therefore, when the plantar flexion or the dorsal flexion of a foot of the person to be assisted is performed, the capability of making the movement of a foot frame follow the movement of a foot of the person to be assisted can be enhanced.

In the seventh to the tenth aspects of the invention described above, a portion of the foot frame which is disposed on the bottom surface of a foot of the person to be assisted may be formed to have a shape of an insole or a shape of an insole with a part thereof cut off (an eleventh aspect of the invention).

The eleventh aspect of the invention enables a person to be assisted to put the foot frame on his or her foot as if he or she were putting on footwear. Further, the person to be assisted can land or leave the foot onto or from a floor in a usual manner as if he or she were not wearing the movement assistance device.

Supplementarily, the movement assistance device in accordance with the present invention may be configured without the foot frames. In such a case, a configuration may be adopted, in which, for example, a lower portion of the lower leg frame is retained, by an appropriate retaining member, such as a belt, to a lower portion of a lower leg of the person to be assisted.

In the first to the eleventh aspects of the invention described above, each knee joint mechanism may adopt a variety of structures, such as a uniaxial joint mechanism having a single joint shaft in the pitch axis direction. In this case, preferably, the following mode can be adopted as a preferred mode of each knee joint mechanism.

Each of the knee joint mechanisms disposed on the outer side and the inner side of a knee of the person to be assisted includes: a first link which is connected, through the intermediary of joint shafts C1a, C1b in the pitch axis direction, to a lower end portion of an X-th main frame, which is one of a first main frame and a second main frame of the thigh frame, and to a part ax, which is one of parts a1 and a2 disposed on the outer side and the inner side of the knee in the lower leg frame so as to be relatively rotatable in the pitch direction with respect to the thigh frame and the lower leg frame, respectively; and a second link which is connected to a lower end portion of the X-th main frame of the thigh frame and to the part ax of the lower leg frame through the intermediary of joint shafts C2a, C2b in the pitch axis direction so as to be relatively rotatable in the pitch direction with respect to the thigh frame and the lower leg frame, respectively, where the X-th main frame is a first main frame for a knee joint mechanism disposed on the outer side of the knee, or a second main frame for a knee joint mechanism disposed on the inner side of the knee.

The part ax is the part a1 disposed on the outer side of the knee for the knee joint mechanism disposed on the outer side of the knee, or the part a2 disposed on the inner side of the knee for the knee joint mechanism disposed on the inner side of the knee.

Further, the joint shafts C1a, C1b, C2a and C2b are disposed such that the following conditions (1) and (2) are satisfied.

Condition (1): The joint shaft C1b is positioned on the front side with respect to the joint shaft C2b.

Condition (2): If the interval between the joint shaft C1a and the joint shaft C1b is denoted by D1, the interval between the joint shaft C2a and the joint shaft C2b is denoted by D2, the interval between the joint shaft C1a and the joint shaft C2a is denoted by Da, and the interval between the joint shaft C1b and the joint shaft C2b is denoted by Db, then D1>Da and D1+Db>D2+Da (a twelfth aspect of the invention).

According to the twelfth aspect of the invention described above, the bending or stretching movement between the thigh frame and the lower leg frame (the relative displacement movement between the thigh frame and the lower leg frame by the movement of the knee joint mechanism) can be performed in virtually the same manner as the bending or stretching movement between a thigh and a lower leg of a person to be assisted (the relative displacement movement between a thigh and a lower leg by the movement of a knee joint of a person to be assisted).

Therefore, when the person to be assisted who is wearing the thigh frame and the lower leg frame bends or stretches his or her leg, the thigh frame and the lower leg frame can move with little relative displacement with respect to a thigh and a lower leg, respectively, of the leg of the person to be assisted.

As a result, it is possible to prevent the knee joint mechanisms from projecting to the front side of the knees of the person to be assisted when the person to be assisted bends his or her legs to a maximum, not to mention when the legs are stretched.

Thus, it is possible to prevent the knee joint mechanisms from coming in contact with a floor and getting in the way when the person to be assisted kneels.

In addition, the synchronization between the movements of the thigh frame and the lower leg frame and the movements of the thigh and the lower leg of the leg of the person to be assisted is enhanced. This makes it possible to prevent or suppress the thigh frame or the lower leg frame from rubbing against the thigh or the lower leg of the leg when the leg is bent or stretched.

In the first to the twelfth aspects of the invention, the joint power generator may adopt a variety of configurations. For example, a mode may be adopted, in which the joint power generator is configured to impart the joint power, through the intermediary of a flexible long member to which a tension is applied, to at least one knee joint mechanism of the knee joint mechanisms on both sides of a knee of the person to be assisted, and the flexible long member is arranged to extend along the first main frame or the second main frame of the thigh frame, which is the main frame connected to the knee joint mechanism to which the joint power is imparted (a thirteenth aspect of the invention).

Accordingly, the flexible long member for imparting the joint power to the knee joint mechanism is arranged along the main frame (the first main frame or the second main frame) connected to the knee joint mechanism. This arrangement makes it possible to prevent a constituent element of the joint power generator, including the flexible long member, from interfering with the movements of the thigh frame and the lower leg frame, or from moving at a place deviating from the thigh frame and the lower leg frame.

Further, the second main frame of the thigh frame is configured to be oblique with respect to a thigh of the person to be assisted, as described above. Hence, the total value of the bending angles of a guide passage, such as a tube, (or the bending angles of the flexible long member) for extending the flexible long member along the second main frame (more specifically, a value obtained by integrating the curvatures of the guide passage in the longitudinal direction of the guide passage over the full length of the guide passage) becomes smaller. As a result, the friction between the flexible long member and the guide passage is reduced.

Further, the movement assistance device according to the twelfth aspect of the invention may adopt a mode in which a flexible long member which is connected to an outer periphery of a part of a first link of at least one knee joint mechanism of the knee joint mechanisms on both sides of a knee of the person to be assisted, the part being adjacent to the joint shaft C1a, and which moves as the first link relatively rotates about the joint shaft C1a, due to bending between the thigh frame and the lower leg frame in a state in which a tension is being applied, is arranged along the first main frame or the second main frame, which is connected to the knee joint mechanism having the first link, and the joint power generator is configured to impart the joint power through the flexible long member to the knee joint mechanism having the first link to which the flexible long member is connected (a fourteenth aspect of the invention).

In the fourteenth aspect of the invention, the phrase "an outer periphery of a part of the first link, the part being adjacent to the joint shaft C1a" means a part of the first link that has an interval with respect to the joint shaft C1a (i.e. a part having a moment arm length with respect to the joint shaft C1a).

In the knee joint mechanism in the twelfth aspect of the invention described above, the amount of a change in the displacement amount of the first link when the leg of the person to be assisted is bent to a maximum from a stretched state is relatively small. According to the fourteenth aspect of the invention, therefore, the required amount of movement of the flexible long member is relatively small. This enables the joint power generator to have a small constitution. In addition, the fourteenth aspect of the invention can provide the same advantages as those of the thirteenth aspect of the invention.

In the first to the fourteenth aspects of the invention, a mode may be adopted, in which the joint power generator includes an elastic member, which generates, at expansion and compression, an elastic force as the joint power to be imparted to at least one knee joint mechanism of the knee joint mechanisms on both sides of a knee of the person to be assisted, and the elastic member is housed inside a first main frame or a second main frame of the thigh frame, which is the main frame connected to the knee joint mechanism to which the elastic force of the elastic member is to be applied, such that the elastic member expands and compresses along the main frame (a fifteenth aspect of the invention).

Thus, the elastic member is housed in the main frame (the first main frame or the second main frame). This arrangement makes it possible to prevent the elastic member from interfering with the movements of the thigh frame and the lower leg frame or from moving at a place deviating from the thigh frame and the lower leg frame. Further, especially when the fourteenth aspect of the invention and the fifteenth aspect of the invention are combined, the required amount of expansion and compression of the elastic member is relatively small. This enables the elastic member to be made small. In addition, the space for housing the elastic member in the first main frame or the second main frame can be reduced.

BRIEF DESCRIPTION OF DRAWINGS

FIG. 4 is a diagram illustrating the configuration and the movement of a knee joint mechanism of the movement assistance device according to the embodiment;

FIG. 5 is a diagram illustrating the configuration of a joint power generator of the movement assistance device according to the embodiment;

FIG. 8A to FIG. 8C are diagrams illustrating a bending movement of a person wearing the movement assistance device according to the embodiment;

DESCRIPTION OF EMBODIMENTS

An embodiment of the present invention will be described with reference to FIG. 1 to FIG. 10.

Figure 1:
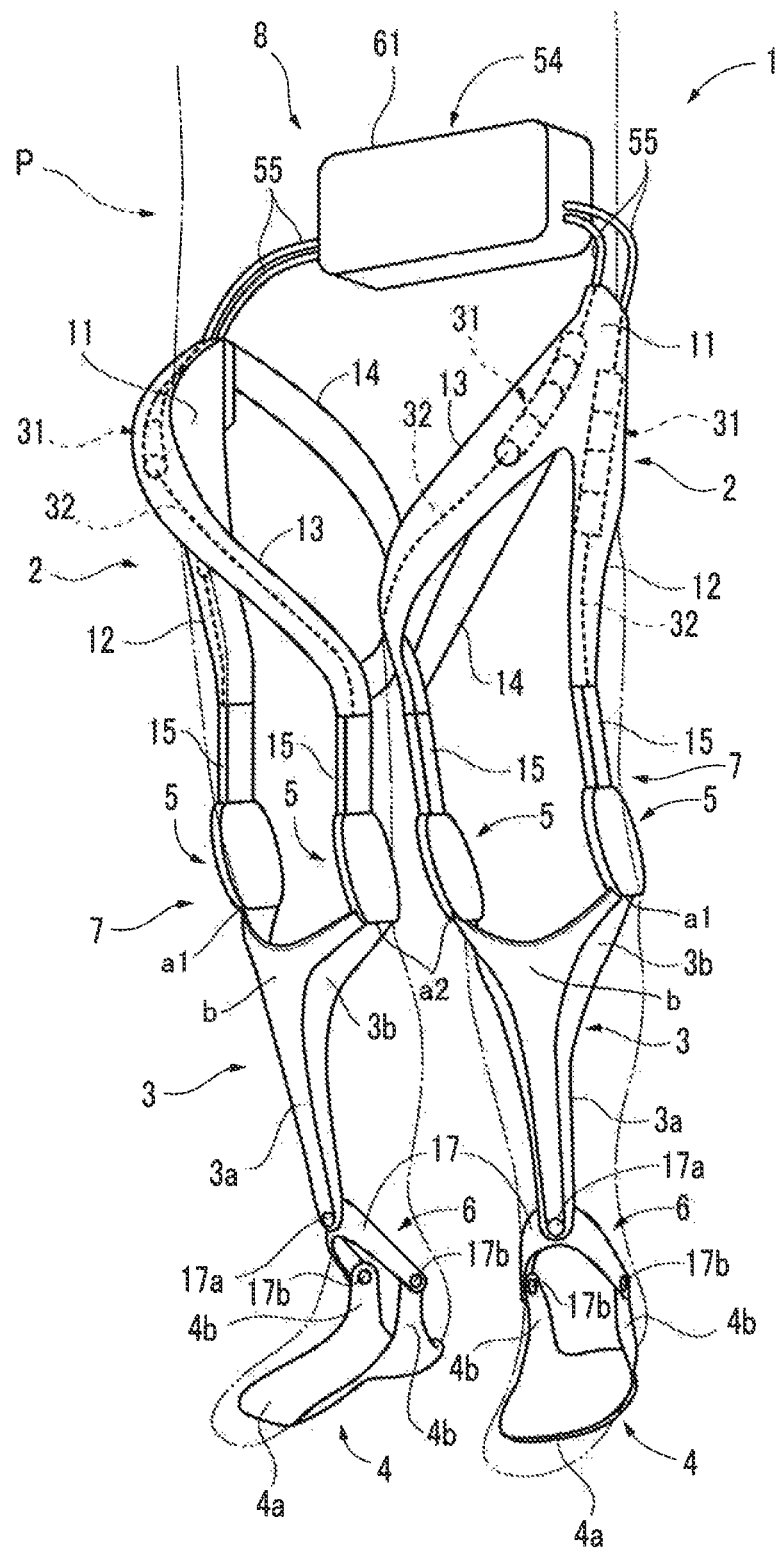
FIG. 1 is a perspective view of a movement assistance device according to an embodiment of the present invention, which is observed from the front side.
Figure 2:
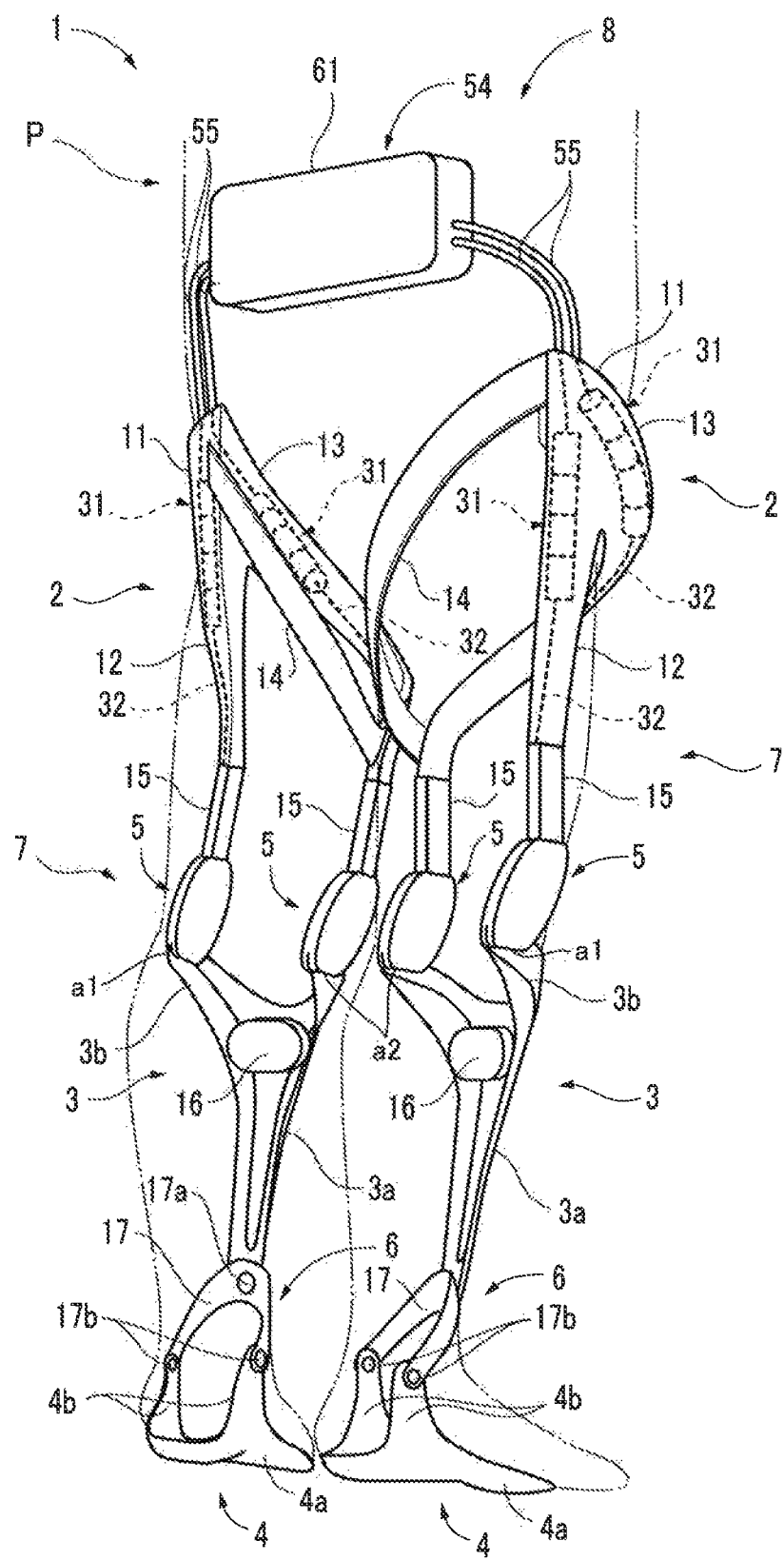
FIG. 2 is a perspective view of the movement assistance device according to the embodiment, which is observed from the rear side.
Figure 3:
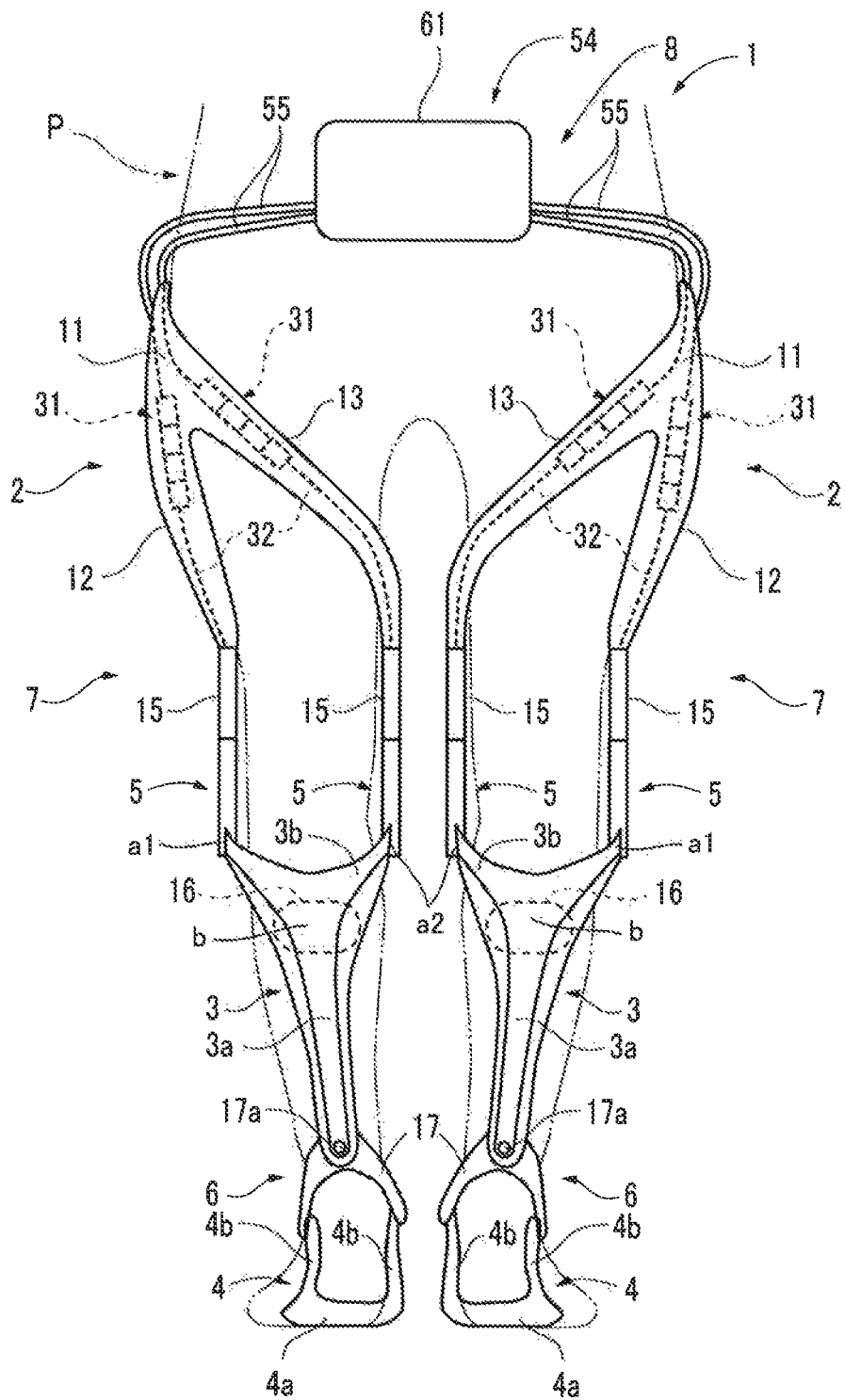
FIG. 3 is a front view of the movement assistance device according to the embodiment.

Referring to FIG. 1 to FIG. 3, a movement assistance device 1, which will be illustrated in the present embodiment, is a device to be attached to a person to be assisted P (human being) so as to assist the movements of the legs mainly when the person to be assisted P walks.

The movement assistance device 1 has, for each leg of the person to be assisted P, a thigh frame 2, a lower leg frame 3, a foot frame 4, a leg link mechanism 7 which includes a pair of knee joint mechanisms 5, 5 connecting the thigh frame 2 and the lower leg frame 3 in a relatively displaceable manner and an ankle joint mechanism 6 connecting the lower leg frame 3 and the foot frame 4 in a relatively displaceable manner, and a joint power generator 8 generating joint power, which is the force to be imparted to the knee joint mechanisms 5, 5 of the leg link mechanism 7.

In FIG. 1 to FIG. 3, for the sake of convenience, the knee joint mechanisms 5 are schematically illustrated like boxes, and the specific configurations of the knee joint mechanisms 5 are not illustrated.

The leg link mechanism 7 for a leg of the person to be assisted P is attached to a leg such that each of the thigh frame 2, the lower leg frame 3, and the foot frame 4 will move integrally with the thigh, the lower leg, and the foot, respectively, of the leg (the right leg or the left leg) to which the leg link mechanism 7 is attached.

The phrase "the thigh frame 2 moves integrally with the thigh of a leg" means that the thigh frame 2 moves together with the thigh of a leg such that the position and the attitude of the thigh frame 2 with respect to the thigh of a leg are maintained to be constant or approximately constant. In this case, a slight change in the position or the attitude of the thigh frame 2 with respect to the thigh of the leg (a slight relative displacement of the thigh frame with respect to the thigh of the leg) caused by the movement of the leg can be tolerated. The same applies to the phrase "the lower leg frame 3 and the foot frame 4 move integrally with the lower leg and the foot, respectively."

The pair of knee joint mechanisms 5, 5 of each of the leg link mechanisms 7 is disposed on both sides (the outer side and the inner side of a knee) the lateral direction (the pitch axis direction) of the knee of a leg of the person to be assisted P in a state in which the leg link mechanism 7 has been attached to the leg of the person to be assisted P.

In the following description, of the knee joint mechanisms 5, 5, the knee joint mechanism 5 disposed on the outer side of a knee may be referred to as the outer knee joint mechanism 5, and the knee joint mechanism 5 disposed on the inner side of the knee may be referred to as the inner knee joint mechanism 5.

Further, in the description of the present embodiment, the inner side and the outer side of each portion (a knee, a thigh and the like) of a leg of the person to be assisted P will mean the side closer to the other leg (the side opposing the other leg) of both sides in the lateral direction of the leg, and the side farther from the other leg. In other words, the inner side and the outer side of the right leg of the person to be assisted P are the left side and the right side, respectively, of the right leg, and the inner side and the outer side of the left leg are the right side and the left side, respectively, of the left leg.

Further, in order to distinguish an element associated with the inner knee joint mechanism 5 and an element associated with the outer knee joint mechanism 5, the words "inner" and "outer" may be added to the name of each element.

Further, in the description of the present embodiment, unless otherwise specified, the lateral direction (or the pitch axis direction), a longitudinal direction (or a roll axis direction), and a vertical direction (or a yaw axis direction) mean the lateral direction, the longitudinal direction, and the vertical direction, respectively, of the person to be assisted P in the state in which the person to be assisted P wearing the movement assistance device 1 is standing up virtually straight. Further, the pitch direction, the roll direction, and the yaw direction mean the direction of rotation about a pitch axis, the direction of rotation about a roll axis, and the direction of rotation about a yaw axis, respectively.

The thigh frame 2 has, as the base frames thereof, a first main frame 12 and a second main frame 13, which are extended from a base 11 in a bifurcated manner. The first main frame 12 and the second main frame 13 are configured to have an integral structure by, for example, a relatively hard resin member.

The first main frame 12 and the second main frame 13 may be structures constructed of a plurality of members connected with each other into single pieces.

The base 11, which is the base portion of the first main frame 12 and the second main frame 13, in the present embodiment is a part disposed on one side of the hip such that the base 11 is positioned higher than the bases on the inner sides of the legs of the person to be assisted P (the portion at which the inner side surfaces of both legs intersect) and lower than the hipbone. The base 11 in the present embodiment forms the upper end portion of the thigh frame 2. In this case, the base 11 (the upper end portion of the thigh frame 2) can be disposed at the foregoing height by appropriately setting the vertical length of the thigh frame 2.

The phrase "one side of the hip" means the right side of the hip as to the thigh frame 2 of the leg link mechanism 7 for the right leg of the person to be assisted P, and the left side of the hip as to the thigh frame 2 of the leg link mechanism 7 for the left leg.

The first main frame 12 is a main frame that connects the base 11 to the outer knee joint mechanism 5. The first main frame 12 is configured to extend to the outer knee joint mechanism 5 from the base 11 in the longitudinal direction of the thigh along the outer side surface of the thigh of the person to be assisted P.

The second main frame 13 is a main frame that connects the base 11 to the inner knee joint mechanism 5. The second main frame 13 is configured to extend from the base 11 to the inner knee joint mechanism 5, passing the front surface side of the thigh of the person to be assisted P (wrapping around toward the front surface side).

Further, the second main frame 13 is configured to extend from the base 11 obliquely with respect to the thigh approximately in a direction toward the inner knee joint mechanism 5, when the second main frame 13 is observed from the front side of the thigh of a leg of the person to be assisted P. In other words, the second main frame 13 is configured to extend from the base 11 to the inner knee joint mechanism 5 aslant with respect to the thigh, inclining obliquely downward, when the second main frame 13 is observed from the front side of the thigh of a leg of the person to be assisted P.

In this case, in an example of the present embodiment, the second main frame 13 is formed such that a portion (an upper portion) adjacent to the base 11 and a portion (a lower portion) adjacent to the inner knee joint mechanism 5 have inclinations (the inclinations observed from the front side of the thigh) with respect to the longitudinal direction of the thigh are smaller than the inclination of a middle portion and that the inclinations continuously and smoothly change.

Further, the second main frame 13 is formed in a curved shape so as to smoothly curve and incline along the curved surface of the front side of the thigh.

Further, in the present embodiment, the first main frame 12 and the second main frame 13 are formed to be hollow to mainly accommodate elastic structures 31, which will be discussed hereinafter.

Further, each of the first main frame 12 and the second main frame 13 has, at the lower end thereof, a hollow joint connecting part 15, which is a part to be connected to the knee joint mechanism 5. The joint connecting part 15 is fixed to the lower portion (a portion on the upper side relative to the joint connecting part 15) of each of the first main frame 12 and the second main frame 13 or formed integrally with the lower portion. The joint connecting parts 15, 15 at the lower ends of the first main frame 12 and the second main frame 13 extend in virtually the same direction (the longitudinal direction of the thigh).

Further, the first main frame 12 and the second main frame 13 are connected to the outer knee joint mechanism 5 and the inner knee joint mechanism 5, respectively, through the intermediary of the joint connecting parts 15 at the lower ends thereof.

In the following description, the joint connecting part 15 at the lower end portion of the first main frame 12 may be referred to as the outer joint connecting part 15, and the joint connecting part 15 at the lower end portion of the second main frame 13 may be referred to as the inner joint connecting part 15.

The thigh frame 2 further includes a body support member 14 extended between the base 11 and a lower portion of the second main frame 13. The body support member 14 is a member that has a function to support a thigh of the person to be assisted P from the rear side of the thigh. The body support member 14 is provided such that the thigh of the person to be assisted P can be inserted between the body support member 14 and the second main frame 13.

More specifically, the body support member 14 is extended between the base 11 and the lower portion of the second main frame 13 such that, when observed from the rear side of the thigh of the person to be assisted P, the body support member 14 inclines with respect to the thigh so as to extend aslant downward from the base 11 toward the lower portion of the second main frame 13 and to curve along a lower part of the buttock of the person to be assisted P and the rear surface of the thigh. Further, one end of the body support member 14 is connected to the base 11, and the other end thereof is connected to the lower part (a part slightly above the inner joint connecting part 15 in the illustrated example) of the second main frame 13.

In this case, the inclination of the body support member 14 with respect to the longitudinal direction of the thigh (the inclination observed from the front side or the rear side of the thigh) is approximately the same as the inclination of the second main frame 13 in the present embodiment.

Further, in the present embodiment, the body support member 14 is formed in a relatively thin strip in order to minimize the discomfort to the person to be assisted P when, for example, sitting on a chair due to the contact between his or her thigh or buttock and the foreign material. Further, the body support member 14 is designed to be less stiff than the first main frame 12 and the second main frame 13. The body support member 14 is made of, for example, a resin member or a fabric member or the like which is softer than the first main frame 12 and the second main frame 13.

The lower leg frame 3 in the present embodiment has a base part 3a disposed to extend in the longitudinal direction of a lower leg on the front side of the lower leg of the person to be assisted P, and a bifurcated part 3b, which is formed integrally with the base part 3a and wraps around both sides (the outer side and the inner side) of a knee of the person to be assisted P from an upper portion of the base part 3a.

Further, of a pair of the distal ends of the bifurcated part 3b, the distal end on the inner side of the knee is connected to the second main frame 13 of the thigh frame 2 through the intermediary of the inner knee joint mechanism 5. Further, the distal end on the outer side of the knee is connected to the first main frame 12 of the thigh frame 2 through the intermediary of the outer knee joint mechanism 5.

The upper portion of the base part 3a (the proximal portion of the bifurcated part 3b) has a relatively large area, and is disposed, covering the upper front surface of the lower leg (specifically, the tibial tuberosity). The upper portion of the base part 3a is a portion subjected to the force of contact with the tibial tuberosity of the lower leg when the person to be assisted P, for example, bends or stretches the leg. Hence, a pad 16 composed of a cushioning member is fixed to the inner surface of an upper portion of the base part 3a, as indicated by the dashed line in FIG. 3. Thus, the upper portion of the base part 3a can be brought in contact with the tibial tuberosity of the person to be assisted P through the intermediary of the pad 16.

Supplementarily, the paired distal ends of the bifurcated part 3b of the lower leg frame 3 correspond to parts a1 and a2 in the present invention. Further, the upper portion of the base part 3a corresponds to a part "b" in the present invention.

The foot frame 4 in the present embodiment is a plate-shaped frame having a bottom plate part 4a placed on the bottom surface side of a foot of the person to be assisted P, the foot being rested on the bottom plate part 4a. The bottom plate part 4a is formed to have a shape which is approximately the same as the shape of a shoe insole or a shape of an insole with a part thereof cut off (e.g. a shape with a front part or a rear part of the insole removed).

Further, the foot frame 4 has rising parts 4b, 4b, which rise from both sides of a portion of the bottom plate part 4a adjacent to the heel. The rising parts 4b, 4b are connected to the lower end portion of the lower leg frame 3 (the lower end portion of the base part 3a) through the ankle joint mechanism 6. The rising parts 4b, 4b are disposed to be positioned on the inner side and the outer side of the heel of the ankle of the person to be assisted P in a state in which a foot of the person to be assisted P is rested on the bottom plate part 4a.

The ankle joint mechanism 6 includes a link member 17, which is disposed surrounding the front periphery of an ankle of the person to be assisted P and which has an approximately semicircular shape (or an approximately U shape). The central portion of the link member 17 is connected to the lower end portion of the lower leg frame 3 through the intermediary of a joint shaft 17a in the roll axis direction.

Further, the link member 17 is journaled to be relatively rotatable in the roll direction about the axis of the joint shaft 17a with respect to the lower leg frame 3.

The joint shaft 17a in the present embodiment is disposed to be positioned above the subtalar joint of the ankle of the person to be assisted P in a state in which the foot of the person to be assisted P is rested on the bottom plate part 4a of the foot frame 4. In the illustrated example, the joint shaft 17a is disposed to be positioned on the upper side of the instep of the foot on the front side of the lower end of the lower leg of the person to be assisted P.

Both ends of the link member 17 are connected to the rising parts 4b of the foot frame 4 through the intermediary of joint shafts 17b in the pitch axis direction (more specifically, of the inner side and the outer side of the malleolus of the person to be assisted P, the rising parts 4b on the same sides as the ends of the link member 17). In this case, the joint shaft 17b on the inner side of the malleolus of the person to be assisted P and the joint shaft 17b on the outer side thereof are coaxially disposed. Further, the link member 17 is journaled to be relatively rotatable about the axes of the joint shafts 171), 17b on the inner side and the outer side (in the pitch direction) with respect to the foot frame 4.

The link member 17 corresponds to the connecting member in the present invention. In this case, the link member 17 is disposed as described above, that is, the link member 17 is disposed to extend in a bifurcated manner to both sides of the malleolus of the person to be assisted P from above the instep of the foot of the person to be assisted P.

A supplementary description will now be given of the axial directions of the joint shafts 17b, 17b on the inner side and the outer side. The rotational axes of the movements of the plantar flexion and the dorsal flexion of the ankle of the person to be assisted P are generally slightly inclined with respect to a plane which is orthogonal to the long axis direction of a tibia (the longitudinal direction of the lower leg).

Therefore, according to the present embodiment, the axes of the joint shafts 17b, 17b of the ankle joint mechanism 6 are slightly inclined with respect to the plane which is orthogonal to the long axis direction of the tibia (the longitudinal direction of the lower leg) of the person to be assisted P such that the axes of the joint shafts 17b, 17b coincide with the rotational axes of the movements of the plantar flexion and the dorsal flexion of the ankle of the person to be assisted P as much as possible. In this case, the axes of the joint shafts 17b, 17b of the ankle joint mechanism 6 are inclined such that the joint shaft 17b on the outer side will be slightly lower than the joint shaft 17b on the inner side in a state in which the bottom plate part 4a of the foot frame 4 is rested on a horizontal plane (or in a state in which the person to be assisted P wearing the movement assistance device 1 is standing on a horizontal plane).

The ankle joint mechanism 6 is configured as described above, so that, at the time of the movements of the plantar flexion or the dorsal flexion of the ankle of the person to be assisted P, the lower leg frame 3 and the foot frame 4 will move integrally with a lower leg and a foot of the person to be assisted P, minimizing the possibility of the occurrence of the relative displacement with respect to the lower leg and the foot.

Further, the joint shaft 17a in the roll axis direction of the ankle joint mechanism 6 is disposed on the upper side of the instep of the foot of the person to be assisted P, thus preventing the foot from interfering with the joint shaft 17a at the time of the plantar flexion movement of the ankle.

In the present embodiment, the ankle joint mechanism 6 does not have a joint shaft in the yaw axis direction (the vertical direction). However, when the foot of the person to be assisted P is rotated in the yaw direction with respect to the lower leg, the base part 3a of the lower leg frame 3 is twisted. This enables the foot frame 4 to relatively rotate in the yaw direction with respect to the lower leg frame 3. Hence, the person to be assisted P can smoothly move his or her foot to any attitude with respect to the lower leg.

However, the ankle joint mechanism 6 may be configured to include a joint shaft in the yaw axis direction.

Both the outer knee joint mechanism 5 and the inner knee joint mechanism 5 are joint mechanisms having the same structure. The knee joint mechanisms 5 in the present embodiment are configured to make it possible to perform the bending and stretching movement of the leg link mechanism 7 (the relative displacement movement between the thigh frame 2 and the lower leg frame 3) by the movements of the knee joint mechanisms 5, 5 in the same movement as the bending and stretching movement of a leg (the relative displacement movement between the thigh and the lower end portion) by a knee joint of an average person.

Referring to FIG. 4, the following will describe the specific configuration of one of the outer knee joint mechanism 5 and the inner knee joint mechanism 5. The configuration of, for example, the outer knee joint mechanism 5 will be representatively described. FIG. 4 illustrates the configuration of the knee joint mechanism 5 and also illustrates how the state of the knee joint mechanism 5 changes when the leg link mechanism 7 is gradually bent from a stretched state.

The outer knee joint mechanism 5 has a first link 21 and a second link 22, which are two links connecting the thigh frame 2 (more specifically, the first main frame 12) and the lower leg frame 3 (more specifically, the outer distal end of the paired distal ends of the bifurcated part 3b).

The first link 21 is connected to the joint connecting part 15 at the lower end portion of the first main frame 12 of the thigh frame 2 through the intermediary of a joint shaft 21a. Further, the first link 21 is also connected to the outer distal end of the bifurcated part 3b of the lower leg frame 3 through the intermediary of a joint shaft 21b. The joint shafts 21a, 21b have axes in the pitch axis direction, which are parallel to each other. Further, the first link 21 is journaled to be relatively rotatable in the pitch direction about the axis of the joint shaft 21a with respect to the thigh frame 2. Further, the first link 21 is also journaled to be relatively rotatable in the pitch direction about the axis of the joint shaft 21b with respect to the lower leg frame 3.

The second link 22 is connected to the joint connecting part 15 at the lower end of the first main frame 12 of the thigh frame 2 through the intermediary of a joint shaft 22a. Further, the second link 22 is also connected to the outer distal end of the bifurcated part 3b of the lower leg frame 3 through the intermediary of a joint shaft 22b. The joint shafts 22a, 22b have axes which are in the same direction (the pitch axis direction) as the direction of the axes of the joint shafts 21a, 21b and which are parallel to each other. Further, the second link 22 is journaled to be relatively rotatable in the pitch direction about the axis of the joint shaft 22a with respect to the thigh frame 2. Further, the second link 22 is also journaled to be relatively rotatable in the pitch direction about, the axis of the joint shaft 22b with respect to the lower leg frame 3.

The joint shaft 21b on the lower leg frame 3 side of the first link 21 and the joint shaft 22b on the lower leg frame 3 side of the second link 22 are disposed such that the joint shaft 22b is positioned on the rear side relative to the joint shaft 21b.

Further, according to the present embodiment, when the bending angle between the thigh frame 2 and the lower leg frame 3 is 0 degrees (when the leg link mechanism 7 is stretched), the joint shaft 22a, on the thigh frame 2 side, of the second link 22 is positioned slightly behind the joint shaft 21a on the thigh frame 2 side of the first link 21.

Further, as illustrated in FIG. 4, there are a total of four joint shafts of the first link 21 and the second link 22, namely, the joint shafts 21a, 21b, 22a and 22b. If the axial interval between the joint shafts 21a and 21b is denoted by D1, the axial interval between the joint shafts 22a and 22b is denoted by D2, the axial interval between the joint shafts 21a and 22a is denoted by Da, and the axial interval between the joint shafts 21b and 22b is denoted by Db, then these axial intervals, D1, D2, Da and Db are set such that the relationships indicated by expressions (1a) to (1c) given below hold.

$$D1 > Da \tag{1a}$$

$$D1 + Db > D2 + Da \tag{1b}$$

$$Da < Db \tag{1c}$$

The first link 21 and the second link 22 are disposed to be staggered in the lateral direction (the direction perpendicular to the plane of paper of FIG. 4) to avoid mutual interference at the time of the betiding movement between the thigh frame 2 and the lower leg frame 3.

The above has described the detailed structure of the outer knee joint mechanism 5. The inner knee joint mechanism 5 has the same structure as the outer knee joint mechanism 5. Further, in the inner knee joint mechanism 5, the joint connecting part 15 at the lower end portion of the second main frame 13 of the thigh frame 2 and the inner distal end of the bifurcated part 3b of the lower leg frame 3 are connected through the intermediary of the first link 21 and the second link 22.

In this case, the first link 21 of the inner knee joint mechanism 5 is journaled to be relatively rotatable by the joint connecting part 15 at the lower end of the second main frame 13 and the inner distal end of the bifurcated part 3b of the lower leg frame 3 through the intermediary of the joint shafts 21a, 21b.

Further, the second link 22 of the inner knee joint mechanism 5 is journaled to be relatively rotatable by the joint connecting part 15 at the lower end of the second main frame 13 and the inner distal end of the bifurcated part 3b of the lower leg frame 3 through the intermediary of the joint shafts 22a, 22b.

Further, the four joint shafts 21a, 21b, 22a and 22b in the inner knee joint mechanism 5 are disposed coaxially with the four joint shafts 21a, 21b, 22a and 22b, respectively, in the outer knee joint mechanism 5.

A supplementary description will now be given of the axial directions of the four joint shafts 21a, 21b, 22a and 22b in each of the knee joint mechanisms 5. For the thigh frame 2 and the lower leg frame 3 to move integrally with the thigh and the lower leg, respectively, of the person to be assisted P with a minimized possibility of the relative displacement with respect to the thigh and the lower leg when the person to be assisted P bends or stretches his or her leg, the axes of the joint shafts 21a, 21b, 22a and 22b of the knee joint mechanisms 5 are preferably slightly inclined with respect to a plane that is orthogonal to the long axis direction of the tibia (the longitudinal direction of the lower leg).

Therefore, according to the present embodiment, the axial directions of the joint shafts 21a, 21b, 22a and 22b of each of the knee joint mechanisms 5 are slightly inclined with respect to the plane that is orthogonal to the longitudinal direction of the lower leg. In this case, the axial directions are inclined such that each of the joint shafts 21a, 21b, 22a and 22b of the inner knee joint mechanism 5 is lower than the joint shafts 21a, 21b, 22a and 22b of the outer knee joint mechanism 5 in a state in which the person to be assisted P wearing the movement assistance device 1 is standing on a horizontal plane.

Supplementarily, the joint shafts 21a, 21b, 22a and 22b of each of the knee joint mechanisms 5 correspond to the joint shafts C1a, C1b, C2a and C2b, respectively, in the present invention. Further, the joint shafts 21a, 21b, 22a and 22b of each of the knee joint mechanisms 5 are disposed as described above. Hence, the joint shafts 21a, 21b, 22a and 22b are disposed to satisfy the foregoing conditions (1) and (2) in the present invention.

Each of the inner knee joint mechanism 5 and the outer knee joint mechanism 5 is configured as described above. Hence, when the leg link mechanism 7 is bent or stretched by the knee joint mechanisms 5, the first link 21 and the second link 22 of each of the knee joint mechanisms 5 move as the degree of bending (the bending angle) of the lower leg frame 3 with respect to the thigh frame 2 increases, as illustrated in FIG. 4.

In this case, when the bending angle of the lower leg frame 3 with respect to the thigh frame 2 increases from the angle (0 degrees) in the state in which the leg link mechanism 7 is stretched, the first link 21 and the second link 22 of each of the knee joint mechanisms 5 move such that the joint shaft 21a on the upper side of the first link 21 moves from a state in which the joint shaft 21a is positioned on the front side relative to a straight line connecting the joint shafts 22a, 22b of the second link 22 to a state in which the joint shaft 21a is positioned on the straight line, and then further moves to the rear side of the straight line.

The movements of the knee joint mechanisms 5 described above make it possible to accomplish the relative displacement movement between the thigh frame 2 and the lower leg frame 3 in the bending or stretching movement of the leg link mechanism 7 in virtually the same form as the form of the relative displacement movement between the thigh and the lower leg in the bending or stretching movement of a leg of the person to be assisted P.

The leg link mechanisms 7 having the structures described above are attached to the person to be assisted P, as illustrated in FIG. 1 and FIG. 2. In this case, the thigh of each leg of the person to be assisted P is inserted between the second main frame 13 of the thigh frame 2 and the body support member 14 of the leg link mechanism 7 that corresponds to the leg, and further, the foot of the leg is rested on the bottom plate part 4a of the foot frame 4 such that the malleolus of the ankle of the leg is positioned between the pair of rising parts 4b, 4b of the foot frame 4. Thus, the leg link mechanism 7 is attached to the person to be assisted P.

When the person to be assisted P wearing the leg link mechanisms 7 as described above moves his or her leg, the thigh frames 2, the lower leg frames 3 and the foot frames 4 of the leg link mechanisms 7 attached to the legs will move integrally with the thighs, the lower legs and the feet, respectively, of the legs.

FIG. 8A to FIG. 8C illustrate an example of the movement of each of the leg link mechanisms 7 when the person to be assisted P wearing the leg link mechanisms 7 bends or stretches his or her legs. FIG. 8A illustrates a state in which the person to be assisted P is standing up straight (a state in which the legs are stretched), FIG. 8C illustrates a state in which the person to be assisted P is squatting (a state in which the legs have been bent almost to a maximum), and FIG. 8B illustrates the legs in a bent state midway between the state in FIG. 8A and the state in FIG. 8C.

In the leg link mechanisms 7 according to the present embodiment, the movements of the knee joint mechanisms 5 having the structures described above make it possible to accomplish the relative displacement movement between the thigh frame 2 and the lower leg frame 3 in the bending or stretching movement of each of the leg link mechanisms 7 in virtually the same form as the form of the relative displacement movement between the thigh and the lower leg in the bending or stretching movement of a leg of the person to be assisted P.

Thus, when a leg of the person to be assisted P is bent or stretched, the bending or stretching movement between the thigh frame 2 and the lower leg frame 3 is performed, causing very little relative displacements of the thigh frame 2 and the lower leg frame 3 with respect to the thigh and the lower leg, respectively, of the leg.

As a result, the knee joint mechanisms 5 will not jut out forward to the front of the knees front the positions on the inner side or outer side of the knees and will be held on the inner side or the outer side of the knees when the degrees of bending of the legs of the person to be assisted P are small and even when the degrees of bending increase, as can be seen from FIG. 8A to FIG. 8C. Therefore, even if the person to be assisted P kneels down, the knee joint mechanisms 5 will not hit a floor, getting in the way.

The knee joint mechanism between the thigh frame 2 and the lower leg frame 3 can be alternatively configured by, for example, a single-axis joint mechanism having the degree of rotational freedom about one axis in the pitch axis direction.

However, in such a case, the thigh frame 2 and the lower leg frame 3 tend to be relatively displaced with respect to the thigh and the lower leg, respectively, due to the mismatch between the movement of the knee joint mechanism and the movement of the knee joint of a leg of the person to be assisted P when the person to be assisted P bends the leg. This frequently causes the person to be assisted P to feel a friction between the thigh frame 2 and the lower leg frame 3 and his or her thigh and lower leg.

In addition, the relative displacement of the thigh frame 2 and the lower leg frame 3 with respect to the thigh and the lower leg, respectively, causes the knee joint mechanism to jut out to the front side of the knee of the person to be assisted P especially when the degree of bending of the leg of the person to be assisted P is increased. Hence, when the person to be assisted P tries to kneel down, the knee joint mechanism tends to hit a floor, getting in the way. This inconvenience can be avoided by the knee joint mechanisms 5 according to the present embodiment.

To put footwear, such as a shoe or a slipper, on a foot of the person to be assisted P, a method may be adopted, in which, for example, the foot of the person to be assisted P with the footwear put thereon is placed together with the footwear on the bottom plate part 4a of the foot frame 4. Another method may be adopted, in which a foot of the person to be assisted P is rested on the bottom plate part 4a of the foot frame 4 and then footwear is attached to the bottom plate part 4a and the foot. Further alternatively, the foot frame 4 can be combined with footwear into one piece (the foot frame 4 is configured as a part of footwear) in advance.

A detailed description will now be given of the joint power generator 8. The joint power generator 8 provided for the leg link mechanisms 7 of the movement assistance device 1 includes two elastic structures 31, 31 configured to generate elastic forces when compressed, flexible long members 32 provided passing through the elastic structures 31, and a tension applying mechanism 33, which variably applies tensions to the flexible long members 32, as illustrated in FIG. 5.

In FIG. 5, for the sake of convenience of illustration, the outer knee joint mechanism 5 and the inner knee joint mechanism 5 are illustrated with the joint shafts thereof oriented in the directions perpendicular to the plane of paper.

The flexible long members 32 are wires (linear members) in the present embodiment and will be hereinafter referred to as the wires 32.

One of the elastic structures 31, 31 is an elastic structure that generates an elastic force providing joint power to be imparted to the outer knee joint mechanism 5 (hereinafter may be referred to as "the outer elastic structure 31"), and the other is an elastic structure that generates an elastic force providing joint power to be imparted to the inner knee joint mechanism 5 (hereinafter may be referred to as "the inner elastic structure 31"). The outer elastic structure 31 and the inner elastic structure 31 share the same structure. An example of the structure will be described with reference to FIG. 6A, FIG. 6B and FIG. 6C.

The elastic structures 31 correspond to the elastic members in the present invention. In the present embodiment, each of the elastic structures 31 has a multilayer structure composed of a plurality of elastic members 41 and a plurality of partition plates 42, which are alternately layered. Further, a through hole 43, which passes through the elastic structure 31 in the direction in which the elastic members 41 and the partition plates 42 are layered, is formed at the axial center portion of the elastic structure 31.

Each of the elastic members 41 in the present embodiment is made of an elastic member, such as single foam (closed cell) rubber sponge, which includes therein numerous hermetically sealed air cells (not illustrated), and is formed in a cylindrical shape. In this case, the axial direction of each of the elastic members 41 coincides with the stacking direction in the elastic structure 31. Further, the through hole of each of the elastic members 41 constitutes a part of the through hole 43 of the elastic structure 31.

Further, the minimum width of the elastic member 41 (the minimum value of the contour width of the elastic member 41 in the direction that is orthogonal to the axial direction of the elastic member 41) is set to be smaller than the total length of the elastic structure 31 in the stacking direction.

Figure 6A:
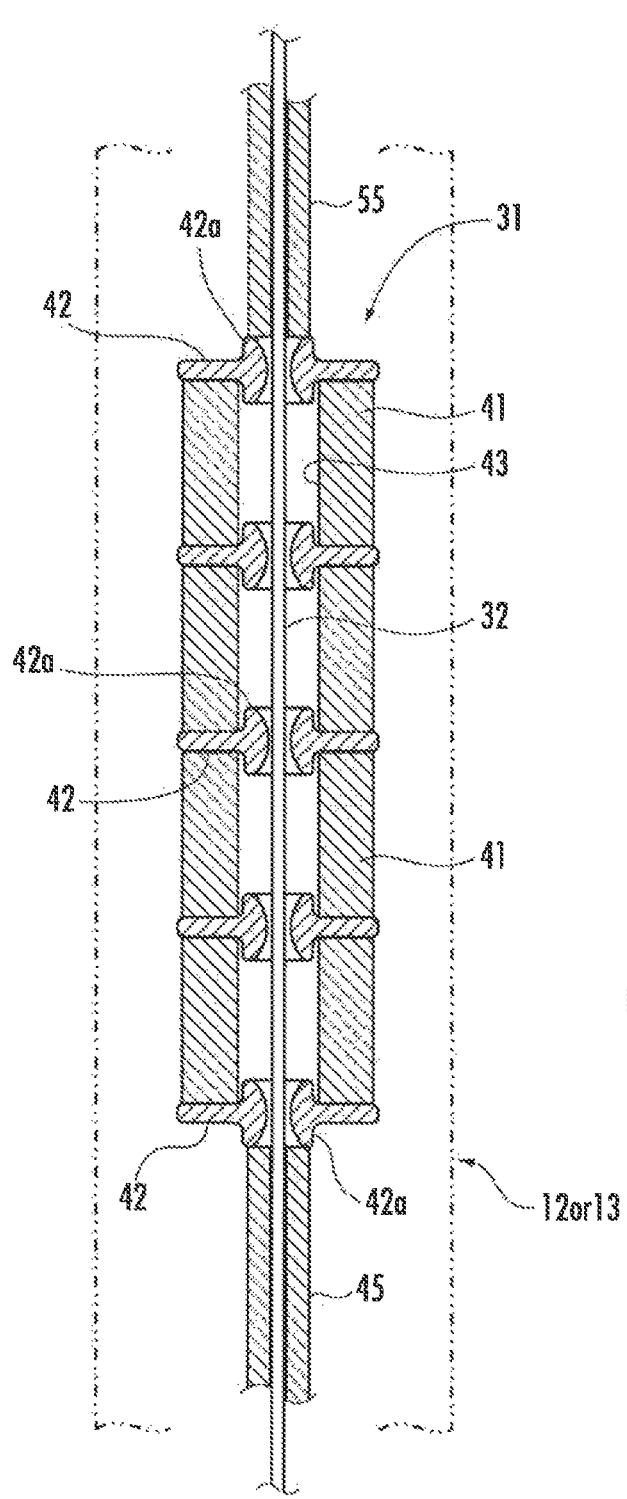
FIG. 6A is a sectional view of an elastic structure provided in the joint power generator illustrated in FIG. 5.
Figure 6B:
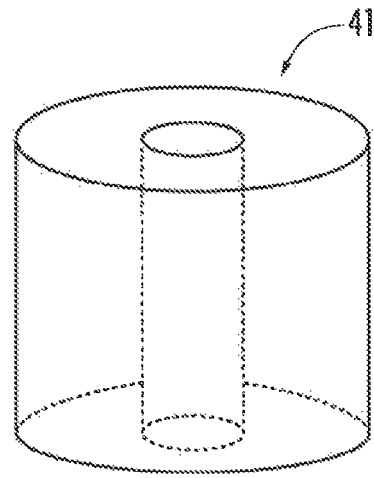
FIG. 6B is a perspective view illustrating an example of an elastic member provided in the elastic structure.

As an example, each of the elastic members 41 may be formed to be cylindrical in a non-compressed state (in a natural state), as illustrated in FIG. 6B. In this case, the outside diameter (diameter) of the elastic member 41 is constant (or virtually constant) in the axial direction of the elastic member 41. Hence, the outside diameter of the elastic member 41 coincides (or virtually coincides) with the minimum width and the maximum width of the elastic member 41. In this case, therefore, the minimum width of the elastic member 41 will be smaller than the total length of the elastic structure 31 in the stacking direction by setting the outside diameter of the elastic member 41 to be smaller than the total length of the elastic structure 31 in the stacking direction.

The partition plates 42 are made of a material, such as a metal or a hard resin or the like having stiffness which is sufficiently higher than that of the elastic members 41, and are formed to be annular. In this case, the axial direction (or the direction of thickness) of the partition plates 42 coincides with the stacking direction of the elastic structure 31. Further, the through holes of the partition plates 42 constitute a part of the through hole 43 of the elastic structure 31.

The external shape and the area of each of the partition plates 42 observed in the axial direction (the direction of thickness) thereof are set such that the whole or virtually whole end surface of the elastic member 41 in the axial direction can be brought in contact with the end surface of the partition plate 42 in the axial direction (the surface on which the elastic member 41 is placed).

Figure 6C:
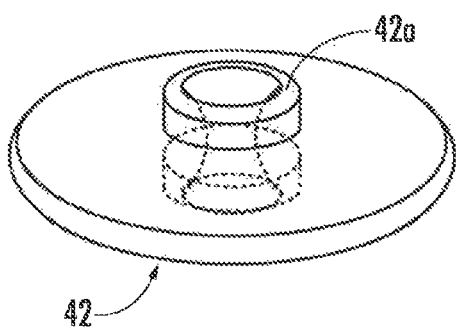
FIG. 6C is a perspective view illustrating an example of a partition plate provided in the elastic structure.

As an example, each of the partition plates 42 may be formed to have an annular shape, as illustrated in FIG. 6C.

Further, the outside diameter (diameter) of the partition plate 42 is set to coincide or virtually coincide with, for example, the outside diameter of the cylindrical elastic member 41, as illustrated in FIG. 6A.

Further, in the present embodiment, a portion 42a adjacent to the inner circumference of the through hole of each of the partition plates 42 is formed to be thicker than a portion around the portion 42a (a portion adjacent to the outer circumference as illustrated in FIG. 6C. The portion 42a (hereinafter referred to as "the thick portion 42a") protrudes on both sides in the direction of thickness (the axial direction) of the partition plate 42. Further, the thick portion 42a of each of the partition plates 42 is formed to have a shape and a size which enable the thick portion 42a to be inserted in the end portion of the through hole of the elastic member 41 to be placed over tine partition plate 42.

For example, if the elastic members 41 have a cylindrical shape, then the thick portion 42a of each of the partition plates 42 may be formed to have an external shape, which is observed in the axial direction of the partition plates 42, such that the external shape (a circular shape in the illustrated example) is accommodated in the cross-sectional shape of the through hole of the elastic member 41 (the shape of the cross-sectional surface that is orthogonal to the axial direction of the elastic member 41), as illustrated in FIG. 6C. In this case, the maximum width (the diameter in the illustrated example) of the thick portion 42a is set to be slightly smaller than the width (inside diameter) of the through hole of the elastic member 41.

Further, in the present embodiment, the minimum value of the cross-sectional area of the through hole of each of the partition plates 42 (the area of the cross-sectional area that is orthogonal to the axial direction of the partition plate 42) is set to be smaller than the minimum value of the cross-sectional area of the through hole of the elastic member 41 (the area of the cross-sectional area that is orthogonal to the axial direction of the elastic member 41).

According to the present embodiment, the inner circumferential surface of the through hole of each of the partition plates 42 is formed to curve such that the cross-sectional area of the through hole changes in the axial direction, as illustrated in FIG. 6C.

More specifically, the inner circumferential surface of the through hole of the partition plate 42 is formed to curve such that the cross-sectional area of the through hole of the partition plate 42 becomes minimum at the middle position (virtually central position) between both ends (both ends in the axial direction) of the thick portion 42a of the partition plate 42, and the cross-sectional area of the through hole of the partition plate 42 increases toward both ends of the thick portion 42a of the partition plate 42. In other words, the inner circumferential surface of the through hole of the partition plate 42 is formed to curve such that the inner circumferential surface becomes narrow at the middle position in the axial direction.

Further, the through hole of the elastic member 41 may be formed such that, for example, the cross-sectional area thereof remains constant in the axial direction. In this case, the minimum value of the cross-sectional area of the through hole of the partition plate 42 (the cross-sectional area at the middle position in the axial direction of the partition plate 42) is set to be smaller than the constant cross-sectional area of the through hole of the elastic member 41.

Further, the inner circumferential surface is formed of a slide material in order to reduce the coefficient of friction between the inner circumferential surface of the through hole of the partition plate 42 and the wire 32. As the slide material, a fluorine resin, a copper alloy (phosphor bronze, brass or the like) or an oil-impregnated metal or the like may be used.

The elastic members 41 and the partition plates 42, which are configured as described above, are alternately layered in a virtually coaxial manner, thereby constituting the elastic structure 31. In this case, the thick portion 42a of each of the partition plates 42 is inserted in the end portion of the through hole of the elastic member 41 placed over the partition plate 42. Further, the through hole 43 of the elastic structure 31 is formed as the hole constituted by the through holes of the elastic members 41 and the through holes of the partition plates 42, which are in mutual communication.

Further, the contact surfaces of the elastic member 41 and the partition plate 42 which overlap each other (more specifically, an end surface of the elastic member 41 and an end surface in the direction of thickness of a portion adjacent to the outer circumference around the thick portion 42a of the partition plate 42 (a portion that is thinner than the thick portion 42a) are firmly attached to each other by, for example, an adhesive agent. The partition plate 42 and the elastic member 41, which overlap each other, can be firmly attached by a method other than bonding. For example, the firm attaching can be accomplished by baking or by integral molding of the partition plate 42 and the elastic member 41.

In the present embodiment, the wire 32 is passed through the through hole 43 of each of the elastic structures 31 configured as described above, and a tension is applied to the wire 32, as will be discussed hereinafter. In a state in which the tension is being applied to the wire 32 passing through the through hole 43 as described above, the elastic structures 31 are compressed in the overlapping direction. In response to the compression, the elastic structure 31 generates the elastic force in a stretching direction. The elastic force increases as the degree of compression of the elastic structure 31 increases.

In the present embodiment, the elastic structures 31 configured as described above are installed to appropriate locations of the leg link mechanisms 7, such as the thigh frames 2. More specifically, the outer elastic structure 31 and the inner elastic structure 31 are accommodated inside the first main frame 12 and inside the second main frame 13, respectively, as indicated by the dashed lines in FIG. 1 to FIG. 3.

In this case, the elastic structures 31 can tolerate a certain degree of curvature caused by the elastic deformation of the elastic members 41. Accordingly, if the place where the elastic structure 31 is to be installed in the first main frame 12 or the second main frame 13 is curved to a certain degree, then the elastic structure 31 can be installed to the place by being curved along the curved contour of the installation place. For example, in the movement assistance device 1 according to the present embodiment, the inner elastic structure 31 is housed in the second main frame 13 while being slightly curved along the curved contour of the second main frame 13, as illustrated in FIG. 1 or FIG. 2.

The tension applying mechanism 33 variably applies a tension to the wire 32 passed through the through hole 43 of the elastic structure 31.

In this case, the tension applying mechanism 33 is configured to transmit a force between the wire 32 and the elastic structure 31 thereby to generate, in the elastic structure 31, an elastic force based on a tension (an elastic force that balances a tension) to be applied to the wire 32 passed through the through hole 43 of the elastic structure 31. Further, the tension applying mechanism 33 is configured such that the tension to the wire 32 and the elastic force of the elastic structure 31 can be changed according to the relative displacement between the thigh frame 2 and the lower leg frame 3 (the bending or stretching movement of the leg link mechanism 7 by the movement of the knee joint mechanism 5). Further, the tension applying mechanism 33 is configured to be capable of applying the elastic force of the elastic structure 31 to the knee joint mechanism 5 as the joint power.

The tension applying mechanism 33 having the foregoing function according to the present embodiment includes: a mechanism retaining a leadout portion of the wire 32, which extends from one end of both ends in the axial direction of the elastic structure 31 (hereinafter may be referred to as "the one-end side leadout portion"), with respect to one end of the elastic structure 31 thereby to maintain the length of the one-end side leadout portion to be constant; a mechanism which maintains a constant distance along a laying path between a middle portion of the laying path of the leadout portion of the wire 32 extended from the other end of the elastic structure 31 (hereinafter may be referred to as "the other-end side leadout portion) and the other end portion of the elastic structure 31; and a mechanism which transmits the relative displacement movement (the bending or stretching movement) of the lower leg frame 3 with respect to the thigh frame 2 to the other-end side leadout portion so as to cause the other-end side leadout portion of the wire 32 to run with respect to the other end portion of the elastic structure 31 according to the relative displacement movement (the bending or stretching movement).

In the present embodiment, the one end of the elastic structure 31 is the upper end of the elastic structure 31 (the end on the opposite side from the end adjacent to the knee joint mechanism 5), and the other end of the elastic structure 31 is the lower end of the elastic structure 31 (the end adjacent to the knee joint mechanism 5).

A specific exemplary configuration of the tension applying mechanism 33 will be described below. Referring to FIG. 5, the tension applying mechanism 33 according to the present embodiment has a long and thin tube 45 provided between the partition plate 42 at the lower end of the outer elastic structure 31 and a partition wall 15a at the upper end of the outer joint connecting part 15 and another long and thin tube 45 provided between the partition plate 42 at the lower end of the inner elastic structure 31 and the partition wall 15a at the upper end of the inner joint connecting part 15, the long and thin tubes 45 being provided inside the first main frame 12 and the second main frame 13, respectively, as the constituent elements of a mechanism which maintains a constant distance along the laying path between the middle portion of the laying path of the other-end side leadout portion of the wire 32 and the lower end portion (the other end portion) of the elastic structure 31. In this case, the partition wall 15a of each of the joint connecting parts 15 corresponds to the middle portion of the laying path of the other-end side leadout portion of the wire 32.

Each of the tubes 45 is a guide tube through which the other-end side leadout portion of the wire 32 from the elastic structure 31 corresponding to the tube 45 is movably passed.

One end of each of the tubes 45 is in contact with (or fixed to) the peripheral edge of an opening end of the through hole of the partition plate 42 at the lower end of the elastic structure 31, and the other end of the tube 45 is in contact with (or fixed to) a predetermined portion of the partition wall 15a at the upper end of the joint connecting part 15. Alternatively, each of the tubes 45 may be fixed to the thigh frame 2 (the first main frame 12 or the second main frame 13).

Further, the interior of each of the tubes 45 is in communication with the through hole 43 of the elastic structure 31. The interior of the tube 45 is also in communication with the interior of the joint connecting part 15 through a hole formed in the partition wall 15a of the joint connecting part 15.

Further, the other-end side leadout portion of the wire 32 from the elastic structure 31 is inserted in the tube 45 connected to the lower end of the elastic structure 31. The other-end side leadout portion of the wire 32 is further passed through the interior of the tube 45 and introduced into the interior of the joint connecting part 15.

The tubes 45 are composed of, for example, a member with high stiffness (a metal, a hard resin or the like). Hence, the tube 45 between the outer elastic structure 31 and the partition wall 15a of the outer joint connecting part 15 maintains the constant distance between the lower end (the other end) of the outer elastic structure 31 and the partition wall 15a of the outer joint connecting section 15 (the distance along the laying path of the wire 32).

Similarly, the tube 45 between the inner elastic structure 31 and the partition wall 15a of the inner joint connecting section 15 maintains the constant distance between the lower end (the other end) of the inner elastic structure 31 and the partition wall 15a of the inner joint connecting section 15 (the distance along the laying path of the wire 32).

Supplementarily, the tubes 45 may use a material having relatively low stiffness with respect to a bending load (a material having flexibility) insofar as the stiffness with respect to a compression load in the longitudinal direction thereof is high.

Further, the mechanism which maintains the constant distance between the middle portion of the laying path of the other-end side leadout portion of the wire 32 and the lower end (the other end) of the elastic structure 31 (the distance along the laying path of the wire 32) is not limited to the tube 45, and may of course use a variety of configurations. For example, a configuration may be adopted, in which the partition plate 42 at the lower end of the outer elastic structure 31 and the partition plate 42 at the lower end of the inner elastic structure 31 are directly fixed to or immovably locked to the first main frame 12 and the second main frame 13, respectively. In this case, the tubes 45 may have low stiffness (may be soft). Alternatively, the tubes 45 may be omitted.

Further, the tension applying mechanism 33 has the first links 21 of the knee joint mechanisms 5 as the constituent elements of a mechanism which transmits the relative displacement movement (the bending or stretching movement) of the lower leg frames 3 with respect to the thigh frames 2 to the other-end side leadout portions of the wires 32 from the elastic structures 31 so as to cause the other-end side leadout portions to move with respect to the lower ends (the other ends) of the elastic structures 31 according to the relative displacement movement. Therefore, the first links 21 of the knee joint mechanisms 5 serve also as the constituent elements of the tension applying mechanism 33.

Specifically, according to the present embodiment, the first link 21 of each of the knee joint mechanisms 5 has the outer peripheral portion thereof (i.e. the portion thereof having an interval (a moment arm length) relative to the joint shaft 21a) formed to function as the outer peripheral portion of a pulley. Further, on each of the outer side and the inner side, the end of the other-end side leadout portion of the wire 32 introduced into the interior of the joint connecting section 15 from the elastic structure 31 is fixed to the outer peripheral portion of the first link 21 of the knee joint mechanism 5.

Thus, as the lower leg frame 3 is relatively displaced with respect to the thigh frame 2 (as the leg link mechanism 7 bends or stretches), the first link 21 of the knee joint mechanism 5 rotates about the axis of the joint shaft 21a with respect to the thigh frame 2. This increases or decreases the winding amount of the other-end side leadout portion of the wire 32 at the first link 21. As a result, the other-end side leadout portion of the wire 32 moves with respect to the lower end of the elastic structure 31 corresponding to the wire 32.

The tension applying mechanism 33 further includes an actuator 54 for controlling the moving operation of the wire 32, and tubes 55, each of which is provided between the partition plate 42 at the upper end of the elastic structure 31 and a casing 61 of the actuator 54, as the constituent elements of a mechanism which retains one-end side leadout portion of the wire 32 from the elastic structure 31 with respect to the upper end (one end) of the elastic structure 31 so as to maintain the length of the one-end side leadout portion to be constant.

The casing 61 of the actuator 54 is attached to the person to be assisted P at a place that will not interfere with the motion of the person to be assisted P. For example, as illustrated in FIG. 1 or FIG. 2, the casing 61 is attached, through the intermediary of a belt or the like (not illustrated), to a place above the waist on the back side of the person to be assisted P such that the casing 61 moves substantially integrally with the upper body of the person to be assisted P. The casing 61 can alternatively be attached to, for example, the back of the person to be assisted P, or attached to the upper body on the abdomen side.

The tubes 55 are guide tubes. Through each of the tubes 55, the one-end side leadout portion of the wire 32 front the elastic structure 31 corresponding to the tube 55 is movably passed.

The tube 55 between the outer elastic structure 31 and the casing 61 is arranged to pass through the interior of the first main frame 12 to the base 11 from the upper end of the outer elastic structure 31, and from the base 11, to pass through a space outside the thigh frame 2 to the casing 61.

Further, the tube 55 between the inner elastic structure 31 and the casing 61 is arranged to pass through the interior of the second main frame 13 to the base 11 from the upper end of the inner elastic structure 31, and from the base 11, to pass through a space outside the thigh frame 2 to the casing 61.

Further, one end of each of the tubes 55 is in contact with (or fixed to) the peripheral edge of an opening end of the through hole of the partition plate 42 at the upper end of the elastic structure 31. The other end of the tube 55 is in contact with (or fixed to) a predetermined portion of an outer wall of the casing 61.

Each of the tubes 55 is formed to be longer than the direct distance between the upper end of the elastic structure 31 and the casing 61 so as to enable the tube 55 to bend between the elastic structure 31 and the casing 61 as the elastic structure 31 is compressed. Further, the tubes 55 are configured to exhibit relatively low stiffness with respect to a bending load and to exhibit relatively high stiffness with respect to a compression load in the longitudinal direction of the tubes 55 (to exhibit resistance to expansion and contraction). Tubes having the same configuration as, for example, a bicycle brake tube (a tube composed of a densely wound metal coil coated with a resin) can be adopted as the tubes 55.

Further, the interior of each of the tubes 55 is in communication with the through hole 43 of the elastic structure 31.

The interior of each of the tubes 55 is also in communication with the interior of the casing 61 through a hole formed in the casing 61.

Further, the one-end side leadout portion of the wire 32 from each of the elastic structures 31 is passed through the tube 55 connected to the upper end of the elastic structure 31. The one-end side leadout portion of the wire 32 is also passed through the interior of the tube 55 and introduced to the interior of the casing 61.

Figure 7:
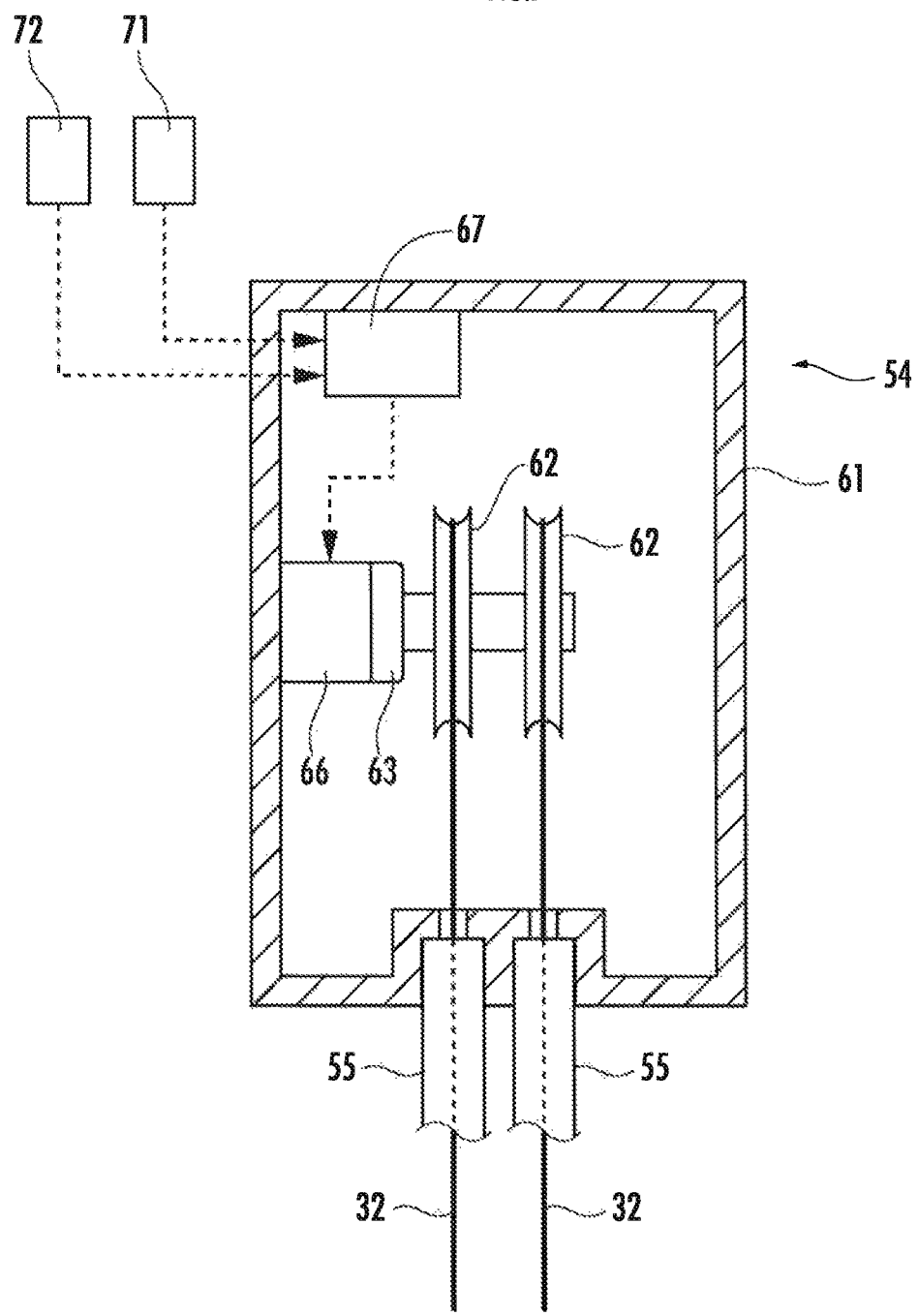
FIG. 7 is a diagram illustrating the configuration of an actuator provided in the joint power generator illustrated in FIG. 5.

As illustrated in FIG. 7, the actuator 54 includes, in the casing 61, two pulleys 62, 62, on which the one-end side leadout portion of the wire 32 from the outer elastic structure 31 and the one-end side leadout portion of the wire 32 from the inner elastic structure 31 are wound, an electric motor 66 capable of rotatively driving the pulleys 62, 62, and a controller 67 which controls the operation of the electric motor 66. Although not illustrated, power supplies (batteries or the like) of the electric motor 66 and the controller 67 are also installed in the casing 61. However, the controller 67 or the power supplies may alternatively be disposed at a location separate from the casing 61 of the actuator 54.

FIG. 7 illustrates only the actuator 54 for one leg link mechanism 7 attached to either the left leg or the right leg of the person to be assisted P. The casing 61 may be shared by the actuator 54 for the leg link mechanism 7 to be attached to the left leg of the person to be assisted P and the actuator 54 for the leg link mechanism 7 to be attached to the right leg, or may be separately provided for each of the two leg link mechanisms 7.

The pulleys 62, 62 are coaxially connected so as to be integrally rotatable. Further, the end of the one-end side leadout portion of the wire 32 from the outer elastic structure 31 and the end of the one-end side leadout portion of the wire 32 from the inner elastic structure 31 are fixed to the outer peripheral portions of the pulleys 62.

Further, the electric motor 66 has the housing thereof (the fixed part of the stator of the electric motor 66) fixed to the casing 61. The pulleys 62, 62 are connected through the intermediary of a speed reducer 63 to the output shaft of the electric motor 66 so as to enable an output torque of the electric motor 66 to be transmitted to the pulleys 62, 62.

The actuator 54 is configured as described above. Hence, the one-end side leadout portion of the wire 32 from the elastic structure 31 is retained with respect to the upper end (one end) of the elastic structure 31 through the intermediary of the casing 61 and the tube 55 such that the length of the one-end side leadout portion is maintained to remain constant when the pulleys 62, 62 are held in a rotation stop state in the casing 61 by the electric motor 66.

The controller 67, which controls the operation of the electric motor 66, is composed of an electronic circuit unit including a CPU, a RAM, a ROM, an interface circuit and the like. The controller 67 may alternatively be composed of a plurality of electronic circuit units that are intercommunicable.

According to the present embodiment, the controller 67 receives detection signals from a rotation sensor 71, which outputs signals based on the rotational angles of the pulleys 62, 62, and from a ground contact sensor 72, which output signals indicating whether the leg link mechanism 7 attached to a leg of the person to be assisted P is in contact with a ground (whether the leg of the person to be assisted P to which the leg link mechanism 7 has been attached is in a supporting leg mode or a free leg mode).

The rotation sensor 71 may be composed of, for example, a rotary encoder, a potentiometer or the like installed to one of the pulleys 62, 62, or the electric motor 66. Further, the ground contact sensor 72 may be composed of, for example, a force sensor or the like, which is installed to the foot frame 4 so as to detect the pressure between the foot frame 4 and a sole of the person to be assisted P.

The controller 67 executes a preinstalled program while monitoring the detection signals from the rotation sensor 71 and the ground contact sensor 72, thereby controlling the operation of the electric motor 66.

A description will now be given of the operation of e movement assistance device 1 according to the present embodiment.

With the leg link mechanisms 7 attached to the legs of the person to be assisted P, as illustrated in FIG. 1 or FIG. 2, the controller 67 is actuated.

For each of the leg link mechanisms 7, the controller 67 controls the operation of the electric motor 66 as described below in response to the detection signals from the rotation sensor 71 and the ground contact sensor 72.

If a detection signal from the ground contact sensor 72 is a signal indicating that the leg link mechanism 7 is not in contact with a ground, i.e. if the leg to which the leg link mechanism 7 has been attached is a free leg (and the foot frame 4 is moving in the air), then the controller 67 controls the output torque of the electric motor 66 so as to impart, to the pulley 62, a small torque (e.g. a torque of a predetermined value) which makes it possible to prevent the wire 32 from slacking.

In this case, if the leg link mechanism 7 is bent or stretched at the knee joint mechanism 5 as the leg to which the leg link mechanism 7 has been attached is bent or stretched, then the wire 32 passing through the elastic structure 31 moves with respect to the elastic structure 31. In this situation, the tension applied to the wire 32 is maintained at a low tension that prevents the slack.

More specifically, if the degree of bending of the leg link mechanism 7 at the knee joint mechanism 5 increases, then the wire 32 passing through the elastic structure 31 is pulled to be wound onto the outer periphery of the first link 21 of the knee joint mechanism 5. This causes the pulley 62 of the actuator 54 to rotate in the direction in which the wire 32 is pulled out. Thus, the wire 32 moves in the direction in which the length of the other-end side leadout portion from the elastic structure 31 increases.

Further, if the degree of bending of the leg link mechanism 7 at the knee joint mechanism 5 decreases, then the wire 32 passing through the elastic structure 31 is pulled out from the outer periphery of the first link 21 of the knee joint mechanism 5. This causes the pulley 62 of the actuator 54 to rotate in the direction in which the wire 32 is rewound. Thus, the wire 32 moves in the direction in which the length of the other-end side leadout portion from the elastic structure 31 decreases.

In the situation in which the wire 32 moves with respect to the elastic structure 31 as the leg link mechanism 7 bends or stretches as described above, the compression load virtually does not act on the elastic structure 31. This leads to a situation in which the elastic force of the elastic structure 31 virtually does not act on the knee joint mechanism 5.

Hence, the person to be assisted P can move the leg acting as the free leg in the same manner as a leg without the leg link mechanism 7 usually moves.

Meanwhile, if a detection signal of the ground contact sensor 72 is a signal which indicates that the leg link mechanism 7 is in contact with a ground, that is, if the leg to which the leg link mechanism 7 has been attached is a supporting leg (and the foot frame 4 is in contact with the ground), then the controller 67 controls the output torque of the electric motor 66 according to a detection signal of the rotation sensor 71 so as to hold the rotational angle of the pulley 62, which is indicated by an output of the rotation sensor 71, at fixed angle (and to hold the pulley 62 in the rotation stop state).

When the output torque of the electric motor 66 is controlled as described above, the one-end side leadout portion of the wire 32 from the elastic structure 31 is locked with respect to the casing 61 through the intermediary of the pulley 62 and the electric motor 66. Further, the one-end side leadout portion of the wire 32 is retained to the partition plate 42 at the upper end of the elastic structure 31 through the intermediary of the casing 61 and the tube 55 in order to maintain the constant length of the one-end side leadout portion.

Figure 9:
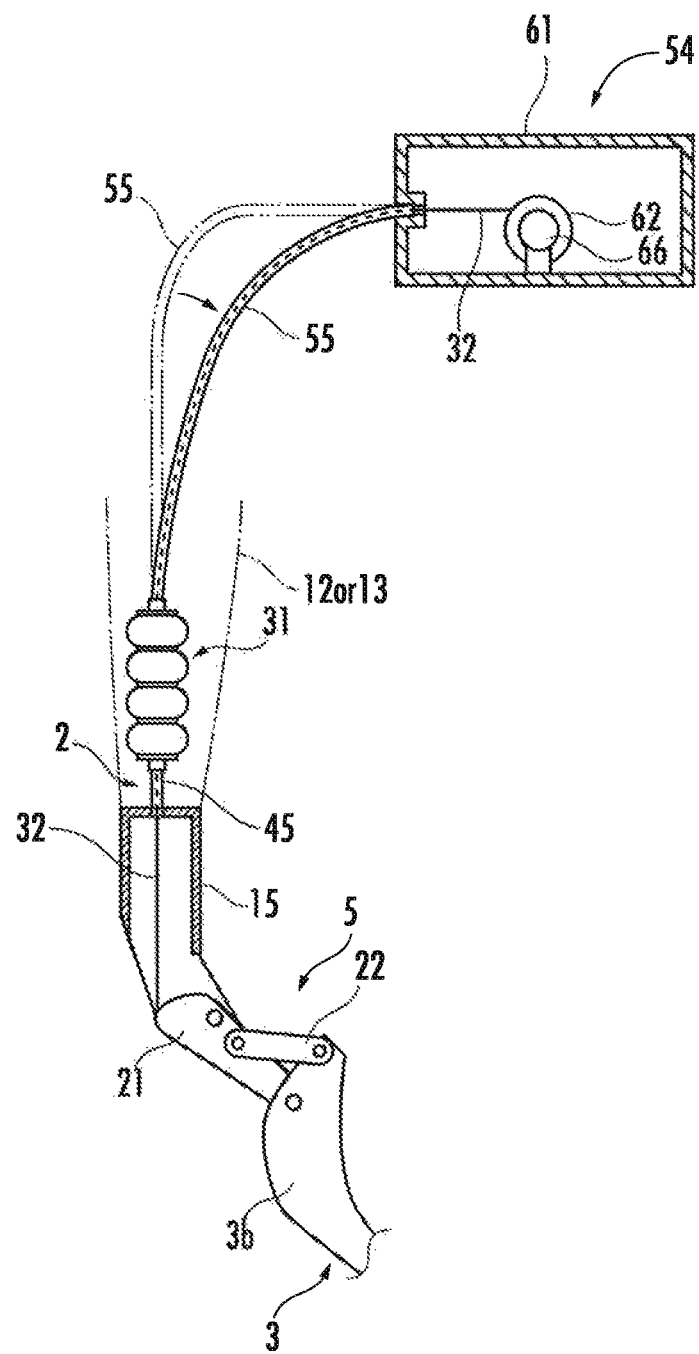
FIG. 9 is a diagram illustrating the operation of the joint power generator illustrated in FIG. 5.

In this state, as the degree of bending of the lower leg frame 3 with respect to the thigh frame 2 increases (as the leg link mechanism 7 is bent at the knee joint mechanism 5 from the stretched state), the tube 55 corresponding to the elastic structure 31 bends and the elastic structure 31 is compressed so as to maintain the constant length of the one-end side leadout portion of the wire 32 from the elastic structure 31, as illustrated in FIG. 9.

At the same time, the output torque of the electric motor 66 is controlled such that the tension to be applied to the wire 32 passing through the elastic structure 31 increases to a tension that balances the elastic force generated by the compression of the elastic structure 31. In this case, the force is transmitted between the wire 32 and the elastic structure 31 through the intermediary of the pulley 62, the electric motor 66, the casing 61 and the tube 55.

With this arrangement, the elastic force of the elastic structure 31 is applied, as the joint power in the direction for stretching the leg link mechanism 7, to the knee joint mechanism 5 on the same side (the outer side or the inner side) as the elastic structure 31. In this case, as the degree of bending between the thigh frame 2 and the lower leg frame 3 increases, the amount of compression of the elastic structure 31 increases and the elastic force eventually increases.

As described above, the joint power from the elastic force of the elastic structure 31 is imparted to the knee joint mechanism 5 of the leg link mechanism 7 of the supporting leg of the person to be assisted P thereby to reduce the load on the supporting leg of the person to be assisted P when, for example, the person to be assisted P walks, stands or sits, squats, or stands up from a squatting position. Thus, a motion (a motion of moving legs) of the person to be assisted P or the like having weakened legs can be assisted.

Figure 10:
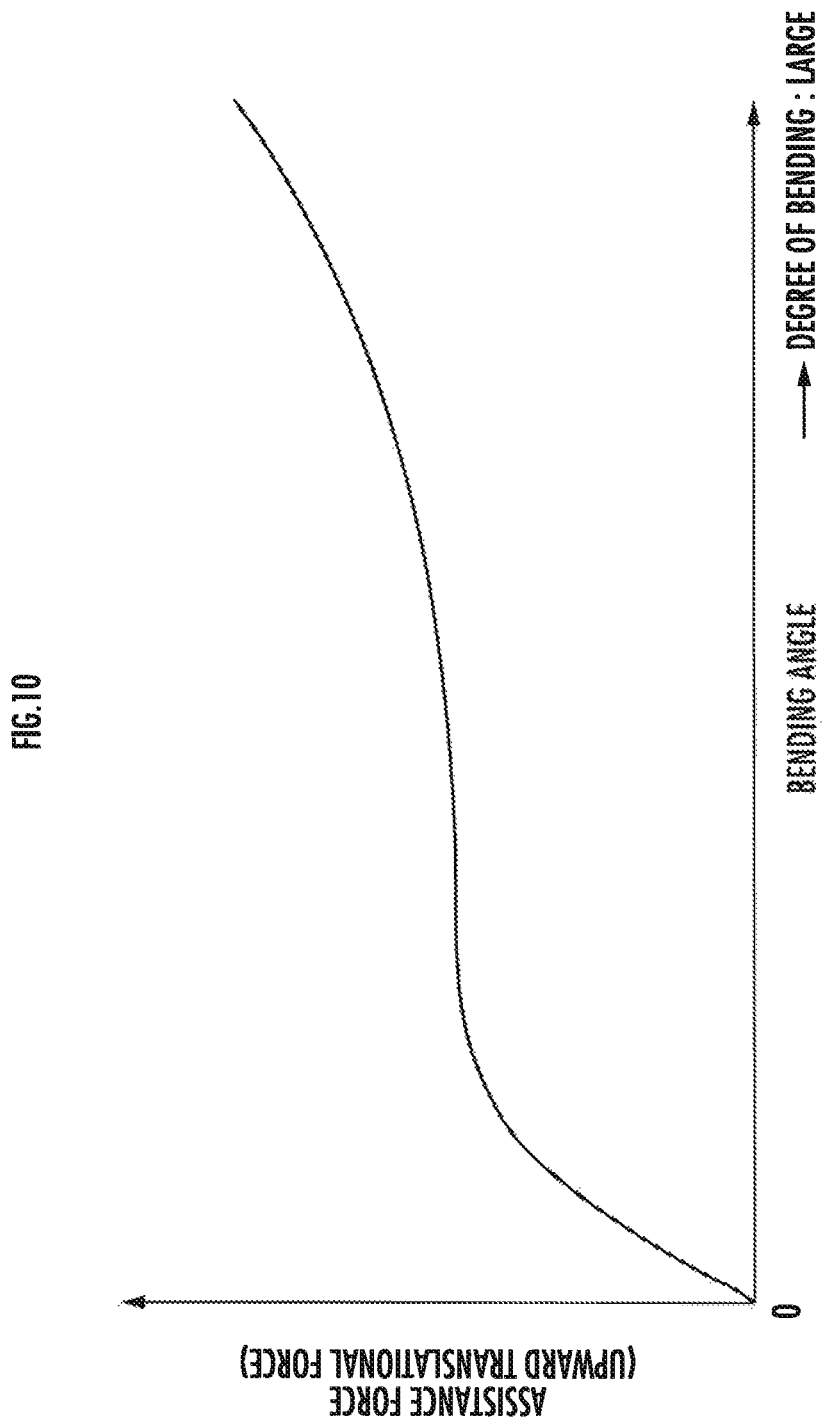
FIG. 10 is a graph illustrating an example of the change characteristics of the assistance force generated in the movement assistance device according to the embodiment.

An example of the operating characteristic exhibited by the movement assistance device 1 according to the present embodiment is illustrated in the graph of FIG. 10. The graph of FIG. 10 is a graph illustrating an example of the relationship between the assistance force acting on the person to be assisted P (the translational force acting upward with respect to the upper body) due to the elastic force of the elastic structure 31 applied to the knee joint mechanism 5 and the degree of bending (the bending angle) between the thigh frame 2 and the lower leg frame 3.

In this example, in the range in which the degree of bending (the bending angle) between the thigh frame 2 and the lower leg frame 3 is relative small (a range in which the leg link mechanism 7 is almost fully stretched), the upward translational force due to the elastic force of the elastic structure 31 increases with high sensitivity in response to an increase in the degree of bending. Then, after the degree of bending increases to a certain level, the upward translational force due to the elastic force of the elastic structure 31 relatively slowly increases as the degree of bending increases.

The operating characteristic of the movement assistance device 1 is not limited to the characteristic illustrated in FIG. 10. A variety of operating characteristics can be implemented by, for example, selecting the elastic characteristic of each of the elastic members 41 of the elastic structure 31, or setting the shape of the outer peripheral portion (the portion that engages with the wire 32) of the first link 21 in the knee joint mechanism 5.

Further, the movement assistance device 1 according to the present embodiment is configured as described above and therefore capable of providing the advantages described below.

The elastic members 41 of the elastic structures 31 are made of single foam (closed cell) rubber sponge or the like, which includes therein numerous hermetically sealed air cells, thus enabling the elastic structures 31 to be lightweight.

Further, the elastic members 41 generate, in addition to the elastic force due to the material thereof, an elastic force due to the compression (the reduction in the volume) of the plurality of air cells in the elastic members 41 (more specifically, the elastic force generated by an increase in the air pressure in the air cells in response to a decrease in the volume of the air cells). This enables each of the elastic structures 31 to increase the elastic force with high sensitivity by the compression in the axial direction thereof. Hence, the elastic structure 31 can generate a relatively large elastic force in spite of its small size.

Further, according to the present embodiment, the elastic structure 31 is formed to have the multilayer structure by the plurality of elastic members 41 and the partition plates 42, and the wire 32, to which a tension is being applied, is passed through the through hole 43 of the elastic structure 31. This arrangement prevents abnormal bending conditions from occurring when the elastic structure 31 is compressed, the abnormal bending conditions including an excessive bending of the entire elastic structure 31 or the bending direction varying for each location in the stacking direction of the elastic structure 31.

Further, according to the present embodiment, the minimum value of the cross-sectional area of the through hole in each of the partition plates 42 of the elastic structure 31 is smaller than the minimum value of the cross-sectional area of the through hole in the elastic members 41. This arrangement prevents or reduces the occurrence of the wire 32 coming in sliding contact with the inner peripheral surface of the through hole in the elastic member 41 even if the elastic structure 31 is installed in the thigh frame 2 in a curved state, causing the wire 32 to deviate from the center of the through hole 43 of the elastic structure 31 or even if the wire 32 deviates from the center of the through hole 43 when the elastic structure 31 is compressed or is expanded from a compressed state. Consequently, the occurrence of the friction between the inner peripheral surface of the through hole in the elastic members 41 and the wire 32 can be prevented or reduced.

In addition, the inner peripheral surface of the through hole in each of the partition plates 42 is curved as described above and formed of a sliding material. Hence, even if the wire 32 comes in sliding contact with the inner peripheral surface of the through holes of the partition plates 42, the force of friction between the wire 32 and the partition plates 42 will be small.

Further, the elastic members 41 and the partition plates 42, which are stacked on each other, are fixed to each other by the contact surfaces thereof. Therefore, friction will not take place at the contact surfaces when the elastic structure 31 is compressed or is expanded from the compressed state.

Thus, it is possible to minimize the possibility of the elastic energy or the like accumulated by the compression of the elastic structure 31 being consumed as the thermal energy due to the friction. This leads to a reduction in energy loss. Further, the elastic energy accumulated in the elastic structure 31 can be efficiently converted to the joint power to be applied to the knee joint mechanism 5.

Further, the portion of each of the partition plates 42, which portion is adjacent to the inner circumference around the through hole, is formed to be the thick portion 42a. In addition, the inner peripheral surface of the through hole on the inner side of the thick portion 32a is curved as described above. Hence, even if the wire 32 comes in contact with the inner peripheral surface of the through hole in the partition plate 42 when the elastic structure 31 is compressed or is expanded from the compressed state, the contact pressure will be spread in the longitudinal direction of the through hole in the partition plate 42. This eventually prevents the pressure of contact between the wire 32 and the partition plate 42 from being locally concentrated in the wire 32 or the partition plate 42. As a result, the durability of the wire 32 or the like can be enhanced by preventing the disconnection, damage or the like of the wire 32.

Further, according to the present embodiment, the base frame of each of the thigh frames 2 is composed of the first main frame 12, which extends from the base 11 disposed on one side of the hip of the person to be assisted P to the outer side of a knee along the outer side of a thigh of the person to be assisted P, and the second main frame 13, which extends from the base 11 obliquely on the front surface side of the thigh to the inner side of the knee.

Thus, there is no frame on the inner side of a place adjacent to the base of a leg of the person to be assisted P. This makes it possible to prevent the thigh frame 2 of the leg link mechanism 7 for the right leg of the person to be assisted P and the thigh frame 2 of the leg link mechanism 7 for the left leg from interfering with each other on the inner sides of the thighs of both legs.

Further, the first main frame 12 of the thigh frame 2 extends in a virtually vertical direction. Further, the second main frame 13 obliquely extends downward from the base 11. The arrangement enables the thigh frame 2 to have relatively high bending stiffness in the pitch direction. Hence, when the person to be assisted P bends his or her legs, a force for pushing up the upper body of the person to be assisted P can be effectively applied to the person to be assisted P through the intermediary of the body support member 14.

Further, the first main frame 12 and the second main frame 13 of the thigh frame 2 can be relatively easily bent to change the interval between the lower portions thereof. This enables the thigh frame 2 to fit to thighs in a wide range of thicknesses. In addition, the possibility of causing the person to be assisted P to feel a sense of constraint can be minimized.

Further, the second main frame 13 of the thigh frame 2 obliquely extends downward from the outer side of the thigh toward the inner side thereof on the front surface side of the thigh. In addition, the second main frame 13 smoothly curves.

With this arrangement, the person to be assisted P sitting on a chair or the like can, for example, easily grasp the portions of the second main frame 13 from the upper side to the lower side while taking a natural posture of his or her arm or the like. Further, in such a grasping state, the person to be assisted P can effortlessly apply a force to the second main frame 13. This enables the person to be assisted P to easily attach or detach the leg link mechanism 7.

Further, the body support member 14 of the thigh frame 2 obliquely extends on the rear surface side of the thigh from the base 11 to the lower end portion of the second main frame 13. Hence, when the leg (the supporting leg) of the person to be assisted P is bent (when the elastic force of the elastic structure 31 is acting on the knee joint mechanism 5), the thigh can be supported from a place on the lower side of the thigh to a place on the upper side thereof by the body support member 14 from the rear surface side.

The base 11, in particular, is a portion disposed at a level that is equal to or higher than the base on the inner side of a leg of the person to be assisted P. Therefore, a thigh of the person to be assisted P can be supported by the body support member 14 extending from the base 11, and a place in the vicinity of a hip joint or a place in the vicinity of an ischial bone can be also supported by the body support member 14.

Thus, the translational force in the direction for pushing up the upper body of the person to be assisted P can be effectively applied to the person to be assisted P while preventing the translational force from being locally applied to any particular portion of the person to be assisted P.

Further, the base 11, which is the upper end portion of the thigh frame 2, is disposed at a level that is equal to or higher than the base on the inner side of a leg of the person to be assisted P, the level being lower than a hipbone of the person to be assisted P. This makes it possible to prevent the upper end portion of the thigh frame 2 from being pressed against the buttocks of the person to be assisted P when a leg of the person to be assisted P is externally rotated, or to prevent the upper end portion of the thigh frame 2 from coining in contact with a side surface of the upper body of the person to be assisted P when the upper body of the person to be assisted P is bent sideways.

Further, according to the present embodiment, the joint power generator 8 applies the elastic force generated by the elastic structure 31 to the knee joint mechanism 5 through the intermediary of the first link 21 of the knee joint mechanism 5. In this case, the knee joint mechanism 5 is configured as described above. Hence, as seen from FIG. 4, even when the person to be assisted P bends each leg to a maximum from a stretched state, the amount of rotational displacement of the first link 21 is relatively small.

Accordingly, the required amounts of expansion and contraction of each of the elastic structures 31 are relatively small. As a result, the space required for placing the elastic structures 31 is smaller. Thus, a higher degree of freedom of placement of the elastic structures 31 can be achieved, and the movement assistance device 1 can be made smaller.

Further, the total value of the bending angles of each of the tubes 55 (more specifically, the value obtained by integrating the curvatures of each of the tubes 55 in the length direction of the tube 55 over the full length of the tube 55) becomes smaller. Hence, the friction between the wire 32 and the tube 55 can be reduced.

[Modifications]

The present invention is not limited to the embodiment described above, and may be implemented in a variety of modes. The following will describe some modifications.

The foregoing embodiment has illustrated the elastic members 41 of the elastic structures 31, which elastic members 41 have a cylindrical shape. However, the shape of the elastic members 41 of the elastic structures 31 is not limited to the cylindrical shape, and may take a variety of other shapes.

Further, a guide tube, which extends in the stacking direction, can be externally inserted onto the elastic structure 31 so that the elastic structure 31 is compressed along the inner peripheral surface of the guide tube.

Further alternatively, in place of the elastic structure 31, a standard elastic member, such as a coil spring, can be used. In this case, for example, a configuration may be adopted, in which the upper end of the coil spring is fixed or locked to the first main frame 12 or the second main frame 13 inside or on the outer side of the first main frame 12 or the second main frame 13, and the lower end of the coil spring is connected to the outer periphery of the first link 21 of the knee joint mechanism through the intermediary of a flexible long member, such as a wire.

Further, in the foregoing embodiment, the wires 32 have been used as the flexible long members. However, the flexible long members may alternatively be belt-shaped or chain-shaped members.

Further, the joint power generator 8 is not limited to the structure described above, and may adopt a variety of other structures. For example, as a tension applying mechanism of the joint power generator 8, a tension applying mechanism 81 having the structure illustrated in FIG. 11 may be adopted.

In the tension applying mechanism 81, the mechanism which maintains a constant distance along the laying path between a middle portion of the laying path of an other-end side leadout portion of a wire 32 from an elastic structure 31 and a second end portion of the elastic structure is the same as the tension applying mechanism 33 of the foregoing embodiment. More specifically, the mechanism includes a thin long tube 45 provided between a partition plate 42 at the lower end of the elastic structure 31 and a partition wall 15a at the upper end of a joint connecting part 15.

Meanwhile, the tension applying mechanism 81 has a locking member 82 fixed to an end of a one-end side leadout portion of the wire 32 as a constituent element of a mechanism that retains the one-end side leadout portion to the upper end (one end) of the elastic structure 31 in order to maintain the constant length of the one-end side leadout portion of the wire 32 from the elastic structure 31. The locking member 82 is abutted against (or fixed to) the peripheral edge of the opening end of a through hole in the partition plate 42 at the upper end of the elastic structure 31.

With this arrangement, the one-end side leadout portion of the wire 32 is retained to the upper end of the elastic structure 31 so as to maintain the constant length of the one-end side leadout portion of the wire 32 (a virtually zero length in this example) under a condition in which a tension is being applied to the wire 32 by pulling the other-end side leadout portion of the wire 32 from the elastic structure 31.

An alternative configuration may be adopted, in which, in place of providing the locking member 82, the one-end side leadout portion of the wire 32 is fixed to the partition plate 42 at the upper end (the one end) of the elastic structure 31 through an appropriate fastening member or an adhesive or the like.

The tension applying mechanism 81 further includes movable pulleys 83 installed to joint connecting parts 15 of thigh frames 2, bearings 84 which rotatably support the movable pulleys 83 around the rotation axes thereof, first links 21 of knee joint mechanisms 5, and an actuator 54 for controlling the moving operation of the wire 32, as the constituent elements of a mechanism which transmits the relative displacement movement (bending and stretching movement) of a lower leg frame 3 with respect to the thigh frame 2 to the other-end side leadout portion of the wire 32 from the elastic structure 31 thereby to cause the other-end side leadout portion to move with respect to the lower end (the other end) of the elastic structure 31 according to the relative displacement movement. The actuator 54 is the same as the one provided in the tension applying mechanism 33 of the foregoing embodiment.

The movable pulleys 83 are housed, together with the bearings 84 which support the movable pulleys 83, in the joint connecting parts 15 so as to be in translational movement toward or away from (in the directions indicated by arrows Y1 and Y2 in FIG. 11) with respect to the first links 21 of the knee joint mechanisms 5.

The movable directions of the movable pulleys 83 and the bearings 84 are restricted by, for example, the inner wall surfaces of the joint connecting parts 15, in which the movable pulleys 83 and the bearings 84 are housed.

Further, the bearings 84 for the movable pulleys 83 are connected to the first links 21 of the knee joint mechanisms 5 through wires 85, which are examples of long members, thereby to be displaced in synchronization with the relative displacement movement (bending and stretching movement) of the lower leg frames 3 with respect to the thigh frames 2.

In this case, one end of the wire 85 on the first link 21 side is fixed to the outer periphery of the first link 21 functioning as the outer periphery of a pulley. Further, the other end of the wire 85 is locked or fixed to the bearing 84.

Thus, as the lower leg frame 3 is relatively displaced (as the leg link mechanism 7 is bent or stretched) with respect to the thigh frame 2, the first link 21 of the knee joint mechanism 5 rotates about the axis of a joint shaft 21a with respect to the thigh frame 2, thereby increasing or decreasing the amount of winding of the wire 85 at the first link 21.

As a result, on the outer side and the inner side, respectively, the relative displacement movement of the lower leg frame 3 with respect to the thigh frame 2 causes the movable pulley 83 and the bearing 84 to move in a translational manner toward or away from the first link 21 of the knee joint mechanism 5. In this case, according to the present embodiment, the amount of winding of the wire 85 at the first link 21 increases as the degree of bending of the lower leg frame 3 with respect to the thigh frame 2 increases. Thus, the movable pulley 83 moves in the translational manner toward the first link 21.

Figure 11:
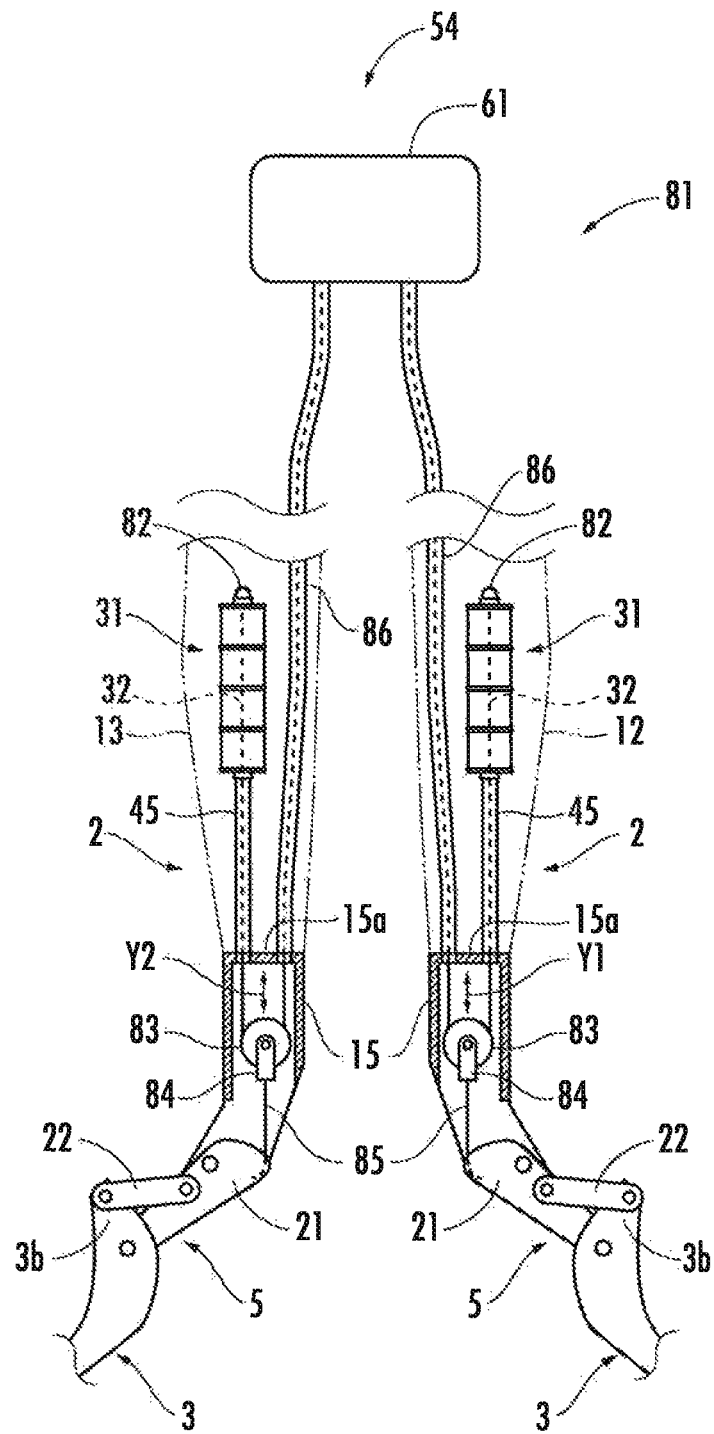
FIG. 11 is a diagram illustrating the configuration of another example of the joint power generator of the movement assistance device according to the embodiment.

The other-end side leadout portion of the wire 32 introduced from the elastic structure 31 into the joint connecting part 15 through the tube 45 is wound on the outer periphery of the movable pulley 83 housed in the joint connecting part 15 (the outer periphery adjacent to the first link 21 of the knee joint mechanism 5), as illustrated in FIG. 11.

Further, the other-end side leadout portion of the wire 32 wound on the outer periphery of the movable pulley 83 in an outer joint connecting part 15 passes through a hole formed in a partition wall 15a of the outer joint connecting part 15 via the outer periphery of the movable pulley 83 and is introduced into an upper portion of the outer joint connecting part 15 of the first main frame 12.

Similarly, the other-end side leadout portion of the wire 32 wound on the outer periphery of the movable pulley 83 in an inner joint connecting part 15 passes through a hole formed in a partition wall 15a of the inner joint connecting part 15 via the outer periphery of the movable pulley 83 and is introduced into an upper portion of the inner joint connecting part 15 of the second main frame 13.

Further, the other-end side leadout portion of the wire 32 of the first main frame 12 and the other-end side leadout portion of the wire 32 of the second main frame 13 pass through a tube 86 of the first main frame 12 and the tube 86 of the second main frame 13, respectively, to reach a casing 61 of the actuator 54, and are introduced into the casing 61 through holes formed in the casing 61. Further, in the casing 61, the wires 32 are connected to the outer peripheries of the foregoing pulleys 62.

In this case, the tube 86 of the first main frame 12 is arranged to extend to a base 11 from the outer joint connecting part 15 in the direction in which the first main frame 12 extends, and to further extend from the base 11 to the casing 61 through a space outside the thigh frame 2.

Further, the tube 86 of the second main frame 13 is arranged to extend to the base 11 from the inner joint connecting part 15 in the direction in which the second main frame 13 extends, and to further extend from the base 11 to the casing 61 through a space outside the thigh frame 2.

Further, as with the tubes 55 of the tension applying mechanism 33 in the foregoing embodiment, the tubes 86 are configured to exhibit relatively low stiffness against a bending load and relatively high stiffness against a compression load in the longitudinal direction of the tubes 86 (being hard to expand and contract).

A tension applying mechanism 81 illustrated in FIG. 11 is configured as described above. In the tension applying mechanism 81, as with the case of the foregoing embodiment, the operation of an electric motor 66 of the actuator 54 is controlled by a controller 67 according to the detection signals of a rotation sensor 71 and a ground contact sensor 72.

In this case, in a state in which the output torque of the electric motor 66 is being controlled such that a small torque that can prevent the wire 32 from slacking (e.g. a torque of a predetermined value) is imparted, if the leg link mechanisms 7 are bent or stretched at the knee joint mechanisms 5, then the movable pulleys 83 in the joint connecting parts 15 are displaced (moved in the translational manner) while rotating in response to the bending or stretching movement. Then, as the movable pulleys 83 are displaced, the pulleys 62 of the actuator 54 (refer to FIG. 7) rotate and a portion of the other-end side leadout portion of the wire 32 from the outer elastic structure 31, the portion being from the outer periphery of the outer movable pulley 83 to the casing 61, and a portion of the other-end side leadout portion of the wire 32 from the inner elastic structure 31, the portion being from the outer periphery of the inner movable pulley 83 to the casing 61, move with respect to the first main frame 12 and the second main frame 13, respectively.

In this situation, virtually no compression load acts on the elastic structures 31. As a result, the elastic forces of the elastic structures 31 virtually do not act on the knee joint mechanisms 5.

Therefore, the person to be assisted P can move the leg acting as the free leg in the same manner as a leg without the leg link mechanism 7 usually moves.

Meanwhile, in a state in which the output torque of the electric motor 66 is being controlled to maintain a constant rotational angle of the pulley 62 (to hold the pulley 62 in the rotation stop state), if the degree of bending of the lower leg frame 3 with respect to the thigh frame 2 is increased, then the movable pulley 83 is displaced (moved in the translational manner) in the direction toward the first link 21 of the knee joint mechanism 5 corresponding thereto.

Then, at this time, as the movable pulley 83 is displaced, the other-end side leadout portion of the wire 32 from the elastic structure 31 is pulled. This causes the compression load to be applied from the wire 32 to the upper end of the elastic structure 31, thus compressing the elastic structure 31. At the same time, the output torque of the electric motor 66 is controlled such that the tension applied to the wire 32 increases to a tension that balances the elastic force generated by the compression of the elastic structure 31.

With this arrangement, as with the case of the foregoing embodiment, the elastic force of the elastic structure 31 is applied, as the joint power in the direction for stretching the leg link mechanism 7, to the knee joint mechanism 5 corresponding to the elastic structure 31.

Further, in this case, the resultant force of the elastic force of the elastic structure 31 and the tension applied to the wire 32 (a force having a magnitude that is approximately double the elastic force) is applied to the knee joint mechanism 5 through the intermediary of the bearing 84 of the movable pulley 83 and the wire 85.

The foregoing tension applying mechanism 81 has been configured using the movable pulleys 83. However, in place of the movable pulleys 83, a differential mechanism, for example, may be used.

Further, the joint power generator 8 may be alternatively configured to, for example, impart the joint power to only one of the outer knee joint mechanism 5 and the inner knee joint mechanism 5.

It is also possible to impart, in place of the elastic force of the elastic structure 31, the driving force of an actuator, such as an electric motor, to both or one of the outer knee joint mechanism 5 and the inner knee joint mechanism 5.

Further, the actuator 54 is not limited to the one in the foregoing embodiment. For example, the electric motor 66 may be replaced by a brake device capable of switching an operation mode between a mode in which the pulleys 62 are braked or locked to be unrotatable and a mode in which the braked or locked state is cleared. Further, a clutch mechanism capable of cutting off the transmission of power between the electric motor 66 and the pulleys 62 may be interposed between the electric motor 66 and the pulleys 62. Further, a pre-tension mechanism which applies a low tension to the wires 32 to prevent the wires 32 from slacking may be provided separately from the electric motor 66 or the brake device.

Further, the structure of the leg link mechanism 7 of the movement assistance device 1 is not limited to the one described above. For example, the knee joint mechanism of the leg link mechanism 7 may be composed of a single-shaft joint mechanism having a degree of freedom of rotation about a single shaft in, for example, the pitch axis direction.

Further, the lower leg frame 3 and the foot frame 4, for example, may have different structures from those in the foregoing embodiment. Further, the curved shape or the like of the thigh frame 2 may be replaced by a different shape from the one in the foregoing embodiment, Further, the leg link mechanism may be configured such that, for example, the ankle joint mechanism 6 and the foot frame 4 of the leg link mechanism 7 are omitted and the lower end portion of the lower leg frame 3 is retained to the ankle of a leg through a belt or the like.

Further, the ankle joint mechanism 6 may be composed of, for example, a free joint or the like.

Further, the base 11 of the thigh frame 2 may alternatively be disposed on the outer side of the upper portion of a thigh.

Further, the body support member 14 may alternatively be disposed to, for example, extend in a lateral direction between the first main frame 12 and the second main frame 13 (in a direction virtually orthogonal to the longitudinal direction of a thigh).

Figure 12:
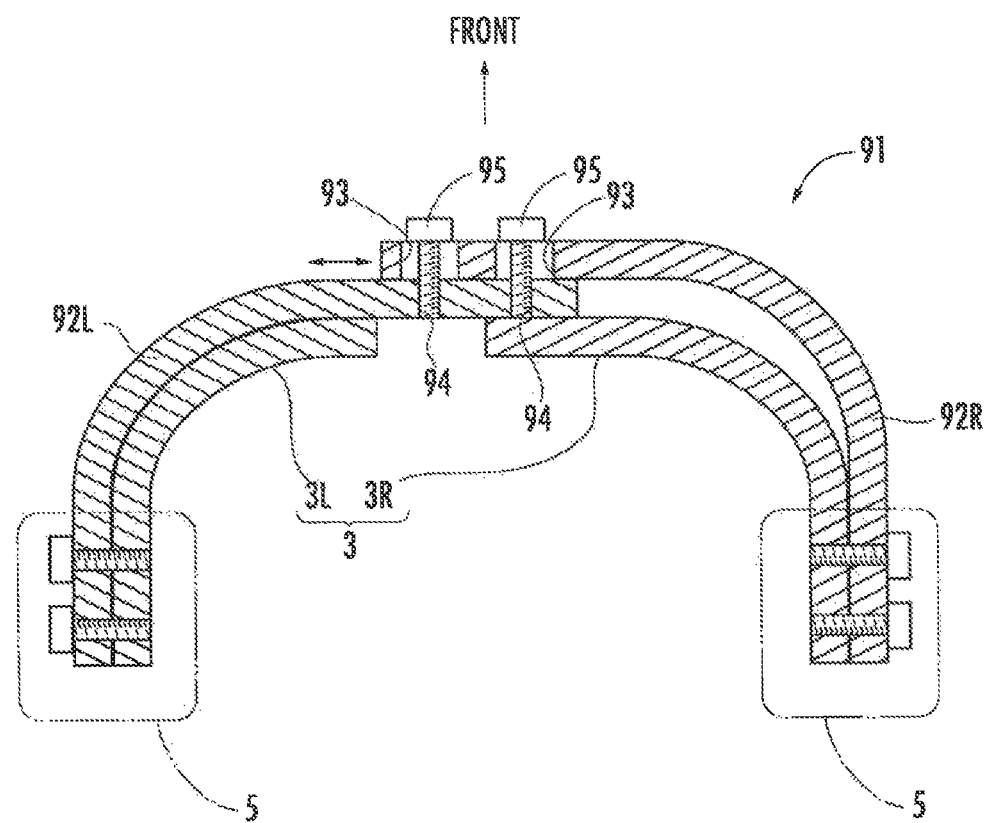
FIG. 12 is a diagram illustrating an example of a mechanism for adjusting the interval between two knee joint mechanisms of the movement assistance device according to the embodiment.

Further, the leg link mechanism 7 may be provided with an adjustment mechanism which adjusts the interval between the outer knee joint mechanism 5 and the inner knee joint mechanism 5. An example of the adjustment mechanism is illustrated in FIG. 12. In FIG. 12, the upper portion of the lower leg frame 3 is illustrated in a cross-sectional view (a cross-sectional view orthogonal to the longitudinal direction of the lower leg frame 3). In this example, the upper portion of the lower leg frame 3 is separated to a left half counterpart 3L and a right half counterpart 3R. The left half counterpart 3L and the right half counterpart 3R are connected at the lower portion of the lower leg frame 3. Further, the connected part is connected to the ankle joint mechanism 6.

In an adjustment mechanism 91, plates 92L and 92R are fastened to the left half counterpart 3L and the right half counterpart 3R, respectively, of the lower leg frame 3. One end of the plate 92L is fastened to the left side of the left half counterpart 3L of the lower leg frame 3. Further, the plate 92L is extended from one end thereof to the front side of the lower leg frame 3.

Further, one end of the plate 92R is fastened to the right side of the right half counterpart 3R of the lower leg frame 3. Further, the plate 92R is extended from one end thereof to the front side of the lower leg frame 3.

Further, the other ends of the plates 92L and 92R are overlapped in the longitudinal direction on the front side of the lower leg frame 3. Further, the plate 92R on the front side is provided with slots 93, 93, which are longer in the lateral direction. In addition, the plate 92L on the rear side is provided with tapped holes 94, 94 approximately matching the slots 93, 93.

Further, screws 95, 95 are screwed in the tapped holes 94, 94 of the plate 92l, on the rear side through the slots 93, 93 of the plate 92R on the front side. The heads of the screws 95, 95 are locked on the surface of the plate 92R on the front side.

In this case, the interval between the outer knee joint mechanism 5 and the inner knee joint mechanism 5 can be adjusted by adjusting the positions of the screws 95 in the slots 93

Figure 13:
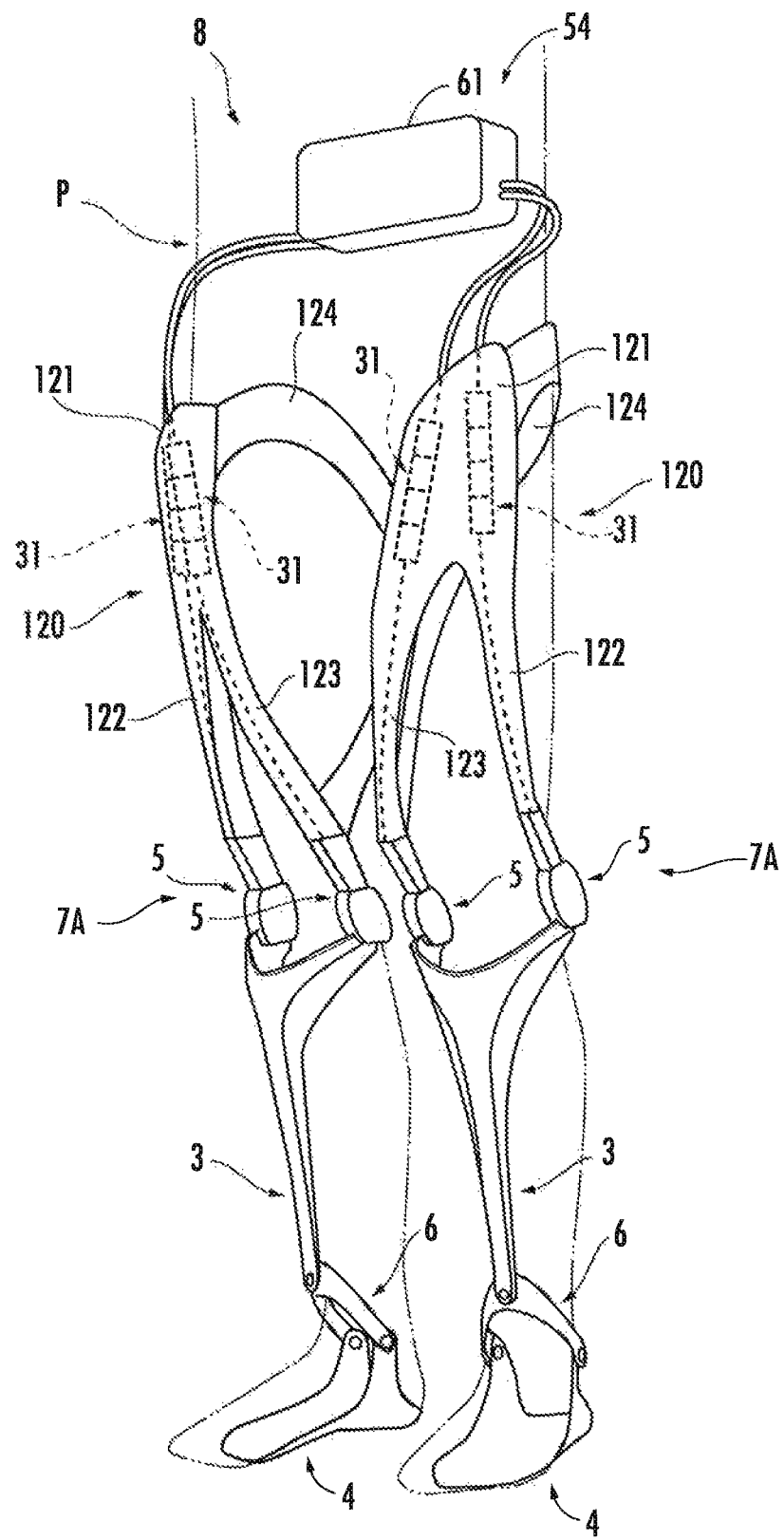
FIG. 13 is a perspective view of another example of the leg link mechanism of the movement assistance device, which is observed from the front side.
Figure 14:
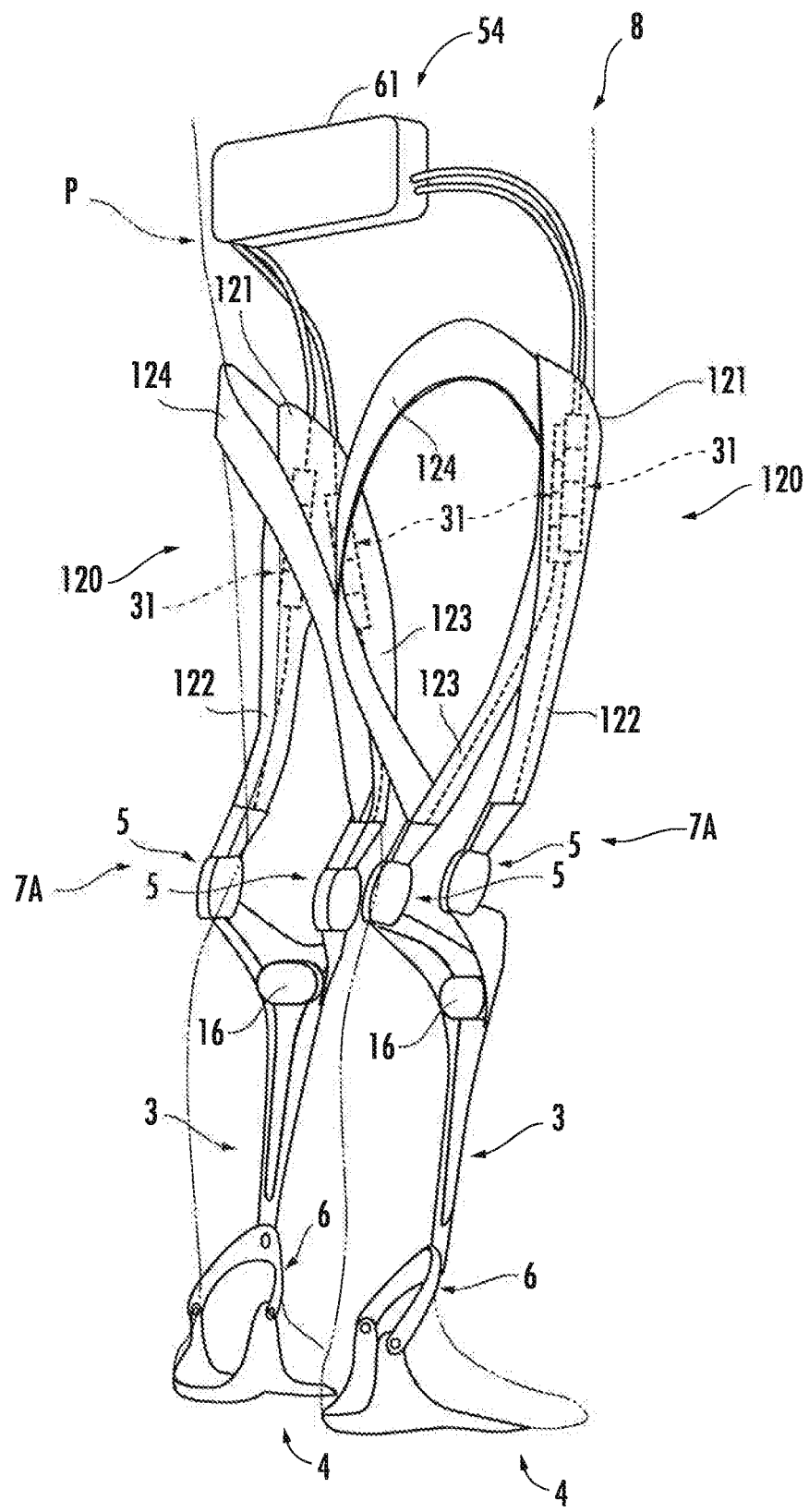
FIG. 14 is a perspective view of another example of the leg link mechanism of the movement assistance device, which is observed from the rear side.

Further, as the structure of the leg link mechanism, the structure illustrated in, for example, FIG. 13 and FIG. 14 can be also adopted.

In this example, a leg link mechanism 7A for each leg of a person to be assisted P differs from the foregoing embodiment only in the structure of a thigh frame 120. In this case, the thigh frame 120 has a base 121 which is disposed at a location adjacent to a side surface on the front surface side of the hip of the person to be assisted P (a location in the direction of approximately 45 degrees with respect to the longitudinal direction and the lateral direction) and on the upper side of a leg, and a first main frame 122 and a second main frame 123, which extend from the base 121 downward in a bifurcated manner.

The first main frame 122 obliquely extends downward from the base 121 toward an outer knee joint mechanism 5 on the front surface side of the thigh of a leg of the person to be assisted P. Further, the first main frame 122 has its lower end portion (a joint connecting part 15) connected to the outer knee joint mechanism 5.

The second main frame 123 obliquely extends downward from the base 121 toward an inner knee joint mechanism 5 on the front surface side of the thigh of the leg of the person to be assisted P. Further, the second main frame 123 has its lower end portion (the joint connecting part 15) connected to the inner knee joint mechanism 5.

Further, the thigh frame 120 has a body support member 124 disposed on the rear surface side of the thigh of a leg of the person to be assisted P. The body support member 124 is extended between the base 11 and the lower end portion of the second main frame 123 such that the body support member 124 extends from the base 11 to the lower end portion of the second main frame 123 via the rear surface of the buttocks of the person to be assisted P.

The leg link mechanism 7A illustrated in FIG. 13 and FIG. 14 has the same structure as that of the leg link mechanism 7 of the foregoing embodiment except for the aspect described above.

In the leg link mechanism 7A having the structure described above, the thigh frame 120 also exhibits high bending stiffness in the pitch direction. Further, imparting the joint power to each of the knee joint mechanisms 5 in the same manner as that of the foregoing embodiment makes it possible to properly apply, to the person to be assisted P, the assistance force in the direction for pushing up the upper body of the person to be assisted P through the intermediary of the body support member 124.

The base 121 is disposed at the place in the direction which is approximately 45 degrees with respect to the longitudinal direction and the lateral direction of the person to be assisted P as described above. This arrangement prevents the base 121 from touching the abdomen of the person to be assisted P when the person to be assisted P squats or the like.

The invention claimed is:

1. A movement assistance device, comprising: a thigh frame; a lower leg frame; a knee joint mechanism which bendably connects the thigh frame and the lower leg frame; and a joint power generator which generates joint power, which is the power to be imparted to the knee joint mechanism, the movement assistance device being attached to a person to be assisted such that the thigh frame and the lower leg frame move integrally with a thigh and a lower leg, respectively, of a leg of the person to be assisted, wherein the knee joint mechanism is composed of an outer joint mechanism on an outer side of a knee and an inner joint mechanism on an inner side of the knee of a leg of the person to be assisted, the thigh frame has a first main frame and a second main frame, which extend in a bifurcated manner, from a base disposed on the outer side of an upper portion of the thigh of the leg of the person to be assisted or on one side of a hip of the person to be assisted and which connect the base to the outer joint mechanism on the outer side of the knee and the inner joint mechanism on the inner side thereof, respectively, and a body support member which is extended between the first main frame or the base and the second main frame, the first main frame is configured to extend from the base in a longitudinal direction of the thigh along an outer side surface of the thigh to the outer joint mechanism on the outer side of the knee, the second main frame is configured to extend from the base to the inner joint mechanism on the inner side of the knee via a front surface side of the thigh, and to extend from the base obliquely with respect to the thigh in a direction toward the inner joint mechanism on the inner side of the knee, as observed from a front side of the thigh, the body support member is configured to extend along a rear surface of the thigh between the base or a first portion lower than the base of the first main frame and a second portion lower than the base of the second main frame, the body support member being in contact with the rear surface, and the first main frame is connected only to the outer joint mechanism on an outer side of a knee and the second main frame is connected only to the inner joint mechanism on an inner side of a knee.

2. The movement assistance device according to claim 1, wherein the second main frame is formed to have a curved shape so as to extend obliquely along a curved surface on a front surface side of the thigh.

3. The movement assistance device according to claim 2, wherein both the first main frame and the second main frame are hollow.

4. The movement assistance device according to claim 1, wherein the lengths in a vertical direction of the first main frame and the second main frame of the thigh frame are set such that the base portion which is an upper end of the thigh frame in a state in which the person to be assisted wearing the movement assistance device is standing up straight is positioned higher than a base on the inner side of the leg of the person to be assisted.

5. The movement assistance device according to claim 1, wherein the length in a vertical direction of the thigh frame is set such that the upper end of the thigh frame in the state in which the person to be assisted wearing the movement assistance device is standing up straight is positioned lower than the hipbone of the person to be assisted.

6. The movement assistance device according to claim 1, wherein the base portion of the thigh frame is a portion disposed on one side of the hip of the person to be assisted, and the body support member is extended between the base portion and a lower end portion of the second main frame such that the body support member is extended from the base portion obliquely with respect to the thigh frame in a direction toward the lower end portion of the second main frame.

7. The movement assistance device according to claim 1, wherein the lower leg frame is formed to have two parts a1 and a2, which are connected to the outer joint mechanism on the outer side and inner joint mechanism on the inner side, respectively, of the knee of a leg of the person to be assisted, and a part "b" which continues to the parts a1 and a2 and are disposed to oppose a tibial tuberosity of the lower leg, the part "b" being provided with a cushioning member which is to be in contact with the tibial tuberosity of the lower leg.

8. The movement assistance device according to claim 1, further comprising:

a plate-shaped foot frame having a part to be disposed on the bottom side of a foot so as to place thereon the foot of the leg of the person to be assisted; and an ankle joint mechanism which connects the foot frame to the lower end portion of the lower leg frame, wherein the lower leg frame is configured to extend in the longitudinal direction of the lower leg at the front side of the lower leg, and the ankle joint mechanism is configured to have a joint shaft which relatively rotates the foot frame in a roll direction with respect to the lower leg frame and which is located above the instep of a foot of the person to be assisted, and joint shafts which relatively rotate the foot frame in a pitch direction with respect to the lower leg frame and which are located on both sides of the ankle of the leg of the person to be assisted.

9. The movement assistance device according to claim 8, wherein the relative rotation of the foot frame in the yaw direction with respect to the lower leg frame is accomplished by twisting of the lower leg frame.

10. The movement assistance device according to claim 8, wherein the ankle joint mechanism includes a connecting member which is disposed to be extending in a bifurcated manner to both sides of an ankle of a person to be assisted from above the instep of a foot of the person to be assisted, and a middle portion between both end portions of the connecting member is connected to a lower end portion of the lower leg frame through the intermediary of a joint shaft in the roll axis direction, and both end portions of the connecting member are connected to the foot frame through the intermediary of a joint shaft in the pitch axis direction.

11. The movement assistance device according to claim 8, wherein the joint shafts in the pitch axis direction of the ankle joint mechanism are joint shafts which are inclined with respect to a horizontal plane such that an outer side of an ankle of the person to be assisted is lower than an inner side thereof in a state in which the foot frame is placed on the horizontal plane.

12. The movement assistance device according to claim 8, wherein a portion of the foot frame which is disposed on the bottom surface of a foot of the person to be assisted is formed to have a shape of an insole or a shape of an insole with a part thereof cut off.

13. The movement assistance device according to claim 1, wherein each of the knee joint mechanisms disposed on the outer side and the inner side of a knee of the person to be assisted includes: a first link which is connected, through the intermediary of joint shafts C1a, C1b in the pitch axis direction, to a lower end portion of an X-th main frame, which is one of a first main frame and a second main frame of the thigh frame, and to a part ax, which is one of parts a1 and a2 disposed on the outer side and the inner side of the knee in the lower leg frame so as to be relatively rotatable in the pitch direction with respect to the thigh frame and the lower leg frame, respectively; and a second link which is connected to a lower end portion of the X-th main frame of the thigh frame and to the part ax of the lower leg frame through the intermediary of joint shafts C2a, C2b in the pitch axis direction so as to be relatively rotatable in the pitch direction with respect to the thigh frame and the lower leg frame, respectively, where the X-th main frame is a first main frame for a knee joint mechanism disposed on the outer side of the knee, or a second main frame for a knee joint mechanism disposed on the inner side of the knee, the part ax is the part a1 disposed on the outer side of the knee for the knee joint mechanism disposed on the outer side of the knee, or the part a2 disposed on the inner side of the knee for the knee joint mechanism disposed on the inner side of the knee, and the joint shafts C1a, C1b, C2a and C2b are disposed such that conditions (1) and (2) given below are satisfied;

Condition (1): The joint shaft C1b is positioned on the front side with respect to the joint shaft C2b, and Condition (2): If a distance between the joint shaft C1a and the joint shaft C1b is denoted by D1, a distance between the joint shaft C2a and the joint shaft C2b is denoted by D2, a distance between the joint shaft C1a and the joint shaft C2a is denoted by Da, and a distance between the joint shaft C1b and the joint shaft C2b is denoted by Db, then D1>Da and D1+Db>D2+Da.

14. The movement assistance device according to claim 13,
wherein a flexible long member which is connected to an outer periphery of a part of a first link of at least one knee joint mechanism of the knee joint mechanisms on both sides of a knee of the person to be assisted, the part being adjacent to the joint shaft C1a, and which moves as the first link relatively rotates about the joint shaft C1a due to bending between the thigh frame and the lower leg frame in a state in which a tension is being applied, is arranged along the first main frame or the second main frame, which is connected to the knee joint mechanism having the first link, and
the joint power generator is configured to impart the joint power through the flexible long member to the knee joint mechanism having the first link to which the flexible long member is connected.

15. The movement assistance device according to claim 1, wherein the joint power generator is configured to impart the joint power, through the intermediary of a flexible long member to which a tension is applied, to at least one knee joint mechanism of the knee joint mechanisms on both sides of a knee of the person to be assisted, and the flexible long member is arranged to extend along the first main frame or the second main frame of the thigh frame, which is the main frame connected to the knee joint mechanism to which the joint power is imparted.

16. The movement assistance device according to claim 1, wherein the joint power generator includes an elastic member, which generates, at expansion and compression, an elastic force as the joint power to be imparted to at least one knee joint mechanism of the knee joint mechanisms on both sides of a knee of the person to be assisted, and the elastic member is housed inside a first main frame or a second main frame of the thigh frame, which is the main frame connected to the knee joint mechanism to which the elastic force of the elastic member is to be applied, such that the elastic member expands and compresses along the main frame.

17. The movement assistance device according to claim 1, wherein the second main frame is formed to curve rigidly along an outer contour of the thigh.

18. The movement assistance device according to claim 17,
wherein both the first main frame and the second main frame are hollow.

19. The movement assistance device according to claim 1, wherein both the first main frame and the second main frame are hollow.

* * * * *